(12) United States Patent
Millar et al.

(10) Patent No.: US 7,846,693 B2
(45) Date of Patent: Dec. 7, 2010

(54) NUCLEIC ACID DETECTION ASSAY

(75) Inventors: Douglas Spencer Millar, Revesby (AU); John Robert Melki, Sans Souci (AU); George L. Gabor Miklos, Newfort (AU)

(73) Assignee: Human Genetic Signatures Pty. Ltd., North Ryde (AU)

( * ) Notice: Subject to any disclaimer, the term of this patent is extended or adjusted under 35 U.S.C. 154(b) by 873 days.

(21) Appl. No.: 10/570,715

(22) PCT Filed: Sep. 3, 2004

(86) PCT No.: PCT/AU2004/001196

§ 371 (c)(1),
(2), (4) Date: Mar. 28, 2007

(87) PCT Pub. No.: WO2005/024053

PCT Pub. Date: Mar. 17, 2005

(65) Prior Publication Data

US 2007/0178459 A1     Aug. 2, 2007

(30) Foreign Application Priority Data

Sep. 4, 2003    (AU) .............................. 2003904832

(51) Int. Cl.
C12P 19/34    (2006.01)
(52) U.S. Cl. ...................................... 435/91.2; 536/24.3
(58) Field of Classification Search .................. None
See application file for complete search history.

(56) References Cited

U.S. PATENT DOCUMENTS

| | | | |
|---|---|---|---|
| 5,629,156 | A | 5/1997 | Shah et al. |
| 5,750,338 | A | 5/1998 | Collins et al. |
| 5,786,146 | A | 7/1998 | Herman et al. |
| 5,824,517 | A | 10/1998 | Cleuziat et al. |
| 5,952,174 | A | 9/1999 | Nikiforov et al. |
| 6,156,501 | A | 12/2000 | McGall et al. |
| 6,251,637 | B1 | 6/2001 | Blusch |
| 6,265,171 | B1 | 7/2001 | Herman et al. |
| 6,331,393 | B1 | 12/2001 | Laird et al. |
| 6,692,918 | B2 | 2/2004 | Kurn |
| 6,960,436 | B2 | 11/2005 | Cottrell |
| 7,008,770 | B1 | 3/2006 | Berlin |
| 7,288,373 | B2 | 10/2007 | Millar et al. |
| 7,413,855 | B2 | 8/2008 | Bergmann et al. |
| 7,504,207 | B2 | 3/2009 | Bergquist |
| 2002/0086324 | A1 | 7/2002 | Laird et al. |
| 2002/0142397 | A1 | 10/2002 | Collas et al. |
| 2003/0073081 | A1 | 4/2003 | Mukai et al. |
| 2003/0082600 | A1 | 5/2003 | Olek et al. |
| 2003/0119025 | A1* | 6/2003 | Olek et al. ............ 435/6 |
| 2003/0143577 | A1 | 7/2003 | Hogrefe et al. |
| 2004/0067559 | A1 | 4/2004 | McCarthy et al. |
| 2004/0086944 | A1 | 5/2004 | Grigg et al. |
| 2004/0203004 | A1 | 10/2004 | Bernard et al. |
| 2004/0219539 | A1 | 11/2004 | Millar et al. |
| 2005/0019762 | A1 | 1/2005 | Olek |
| 2005/0059003 | A1 | 3/2005 | Enoki et al. |
| 2005/0118578 | A1 | 6/2005 | Mineno et al. |
| 2005/0202490 | A1 | 9/2005 | Makarov |
| 2006/0014144 | A1 | 1/2006 | Christensen et al. |
| 2006/0051771 | A1 | 3/2006 | Murphy et al. |
| 2006/0166203 | A1 | 7/2006 | Took |
| 2006/0286576 | A1 | 12/2006 | Lofton-Day |
| 2007/0020633 | A1 | 1/2007 | Millar |
| 2007/0020639 | A1 | 1/2007 | Shapero |
| 2007/0020653 | A1 | 1/2007 | Holliger |
| 2007/0026070 | A1 | 2/2007 | Vonwiller |
| 2007/0042365 | A1 | 2/2007 | Millar et al. |
| 2007/0065824 | A1 | 3/2007 | Gutig |
| 2007/0178457 | A1 | 8/2007 | Millar |
| 2007/0190530 | A1 | 8/2007 | Birkner et al. |
| 2007/0264653 | A1 | 11/2007 | Berlin et al. |
| 2008/0050738 | A1 | 2/2008 | Millar |
| 2009/0029346 | A1 | 1/2009 | Millar et al. |
| 2009/0042732 | A1 | 2/2009 | Millar |
| 2009/0130657 | A1 | 5/2009 | Millar |
| 2009/0263909 | A1 | 10/2009 | Millar |
| 2010/0041013 | A1 | 2/2010 | Millar et al. |
| 2010/0092972 | A1 | 4/2010 | Millar et al. |

FOREIGN PATENT DOCUMENTS

DE    103 31 107  B3    12/2004

(Continued)

OTHER PUBLICATIONS

Badal Sushma et al.: "The human papillomavirus-18 genome is efficiently targeted by cellular DNA methylation" VIROLOGY, vol. 324, No. 2, Jul. 1, 2004, pp. 483-492.

(Continued)

Primary Examiner—Heather Calamita
(74) Attorney, Agent, or Firm—Knobbe, Martens, Olson & Bear, LLP

(57) ABSTRACT

A method for determining the methylation status of a potential methylation site in genomic nucleic acid comprising treating genomic nucleic acid with an agent which modifies cytosine bases but does not modify 5methyl-cytosine bases under conditions to form a. modified nucleic acid template containing a potential methylation site; providing a first clamp containing a first capture sequence complementary to a region flanking one side of the potential methylation site in the modified nucleic acid template, providing a second clamp containing a second capture sequence complementary to a region flanking the other side of the potential methylation site in the modified nucleic acid template; allowing the first clamp and the second clamp to hybridise to the modified nucleic acid template; ligating the hybridised first and second clamps to form a probe spanning the potential methylation site in the modified nucleic acid template; digesting the modified nucleic acid template to obtain the probe; and detecting the probe and determining the methylation status of the potential methylation site in the modified genomic nucleic acid.

41 Claims, 13 Drawing Sheets

FOREIGN PATENT DOCUMENTS

| | | |
|---|---|---|
| EP | 1 130 113 | 9/2001 |
| EP | 1 319 718 | 6/2003 |
| EP | 1443052 | 8/2004 |
| EP | 1 801 213 A2 | 6/2007 |
| WO | WO 95/01456 | 1/1995 |
| WO | WO 95/22623 | 8/1995 |
| WO | WO 97/41254 | 11/1997 |
| WO | WO 97/45559 | 12/1997 |
| WO | WO 98/20157 | 5/1998 |
| WO | WO 98/29108 | 7/1998 |
| WO | WO 99/09211 A2 | 2/1999 |
| WO | WO 99/14226 | 3/1999 |
| WO | WO 99/49081 A2 | 9/1999 |
| WO | WO 00/44934 | 8/2000 |
| WO | WO 00/50869 A2 | 8/2000 |
| WO | WO 01/09374 A2 | 2/2001 |
| WO | WO 01/38565 A2 | 5/2001 |
| WO | WO 01/42493 A2 | 6/2001 |
| WO | WO 01/76451 A2 | 10/2001 |
| WO | WO 02/36821 A2 | 5/2002 |
| WO | WO 02/38801 | 5/2002 |
| WO | WO 02/46452 | 6/2002 |
| WO | WO 02/072880 | 9/2002 |
| WO | WO 02/097065 | 12/2002 |
| WO | WO 2003/008623 A2 | 1/2003 |
| WO | WO 2003/048732 | 6/2003 |
| WO | WO 2003/051901 A2 | 6/2003 |
| WO | WO 2003/052132 A2 | 6/2003 |
| WO | WO 2003/052133 A2 | 6/2003 |
| WO | WO 2003/052134 A2 | 6/2003 |
| WO | WO 2004/015139 | 2/2004 |
| WO | WO 2004/065625 | 8/2004 |
| WO | WO 2004/090166 | 10/2004 |
| WO | WO 2004/096825 | 11/2004 |
| WO | WO 2004/111266 | 12/2004 |
| WO | WO 2005/021778 | 3/2005 |
| WO | WO 2005/056790 A1 | 6/2005 |
| WO | WO 2006/058393 | 6/2006 |
| WO | WO 2006/066353 | 6/2006 |
| WO | WO 2006/113770 A1 | 10/2006 |
| WO | WO 2007/106802 A2 | 9/2007 |
| WO | WO 2008/109945 | 9/2008 |
| WO | WO 2008/135512 A2 | 11/2008 |
| WO | WO 2009/067743 | 6/2009 |
| WO | WO 2009/070843 | 6/2009 |
| WO | WO 2009/079703 | 7/2009 |

OTHER PUBLICATIONS

Badal V. et al.: "CpG methylation of human papillomavirus type 16 DNA in cervical cancer cell lines and in clinical specimens: Genomic hypomethylation correlates with carcinogenic progression" Journal Of Virology, The American Society For Microbiology, US, vol. 77, No. 11, Jun. 1, 2003, pp. 6227-6234.

Baleriola C et al.: "Comparison of a novel HPV test with the Hybrid Capture II (hcII) and a reference PCR method shows high specificity and positive predictive value for 13 high-risk human papillomavirus infections" Journal of Clinical Virology, Elsevier, Amsterdam, NL, vol. 42, No. 1, May 1, 2008, pp. 22-26.

Extended European Search Report issued in corresponding European Application No. 05821631.8, dated Nov. 7, 2008.

Feng et al: "Detection of hypermethylated genes in women with and without cervical neoplasia." Journal of the National Cancer Institute Feb. 16, 2005, vol. 97, No. 4, pp. 273-282.

Gu W. et al, Depletion of Saccharomyces cerevisiae tRNAHis Guanylyltransferase Thglp leads to uncharged tRNAH is with additional m5C, Mol Cell Biol. Sep. 2005; vol. 25, No. 18, pp. 8191-8201.

International Search Report issued for corresponding PCT Application No. PCT/AU2006/000755, dated Aug. 30, 2006.

International Search Report issued on corresponding PCT Application No. PCT/AU2008/000367, dated May 14, 2008.

Kalantari, Mina et al. "Conserved methylation patterns of human papillomavirus type 16 DNA in asymptomatic infection and cervical neoplasia," Journal of Virology, vol. 78, No. 23, Dec. 2004, pp. 12762-12772.

Kim T Y et al: "DNA hypermethylation in gastric cancer" Alimentary Pharmacology & Therapeutics, vol. 20, No. Suppl. 1, Jul. 2004, pp. 131-142.

Kozak et al.: "Influence of secondary structure on binding and migration of 40S ribosomal subunits," Cell, vol. 19, 1980, pp. 79-90.

Malyukova A V et al: "Methylation of the Putative Tumor Suppressor Gene RASSF1A in Primary Cervical Tumors" Molecular Biology, Kluwer Academic Publishers-Plenum Publishers, NE, vol. 38, No. 6, Nov. 1, 2004, pp. 857-864.

Narayan Gopeshwar et al: "Frequent Promoter Methylation of CDH1, DAPK, RARB, and HIC1 Genes in Carcinoma of Cervix Uteri: Its Relationship to Clinical Outcome" Molecular Cancer, Biomed Central, London, GB, vol. 2, No. 1, May 13, 2003, p. 24.

Nilsson et al., "Padlock Probes: Circularizing Oligonucleotides for localized DNA Detection", Science; 265:2085-2088 (1994).

Nousbaum, J. et al., "Prospective Characteristics of Full-Length Hepatitis C Virus NS5A Quasispecies during Induction and Combination Antiviral Therapy," Journal of Virology, 74, No. 19, pp. 9028-9038 (2000).

Office Action in U.S. Appl. No. 10/543,017 dated Dec. 8, 2008.
Office Action in U.S. Appl. No. 10/543,017 dated Jun. 20, 2008.
Office Action in U.S. Appl. No. 10/543,017 dated Oct. 19, 2007.
Office Action in U.S. Appl. No. 11/573,873 dated May 4, 2009.
Office Action in U.S. Appl. No. 11/660,586 dated Sep. 15, 2009.

Supplementary European Search Report issued in corresponding European Application No. 05779000.8, dated Nov. 24, 2008.

Supplementary European Search Report issued on corresponding European Patent Application No. EP 05 81 3335, dated Mar. 12, 2009.

Supplementary European Search Report issued on corresponding European Patent Application No. EP 06 77 4977, dated Jul. 28, 2009.

Ushijima Toshikazu et al: "Aberrant methylations in cancer cells: Where do they come from?" Cancer Science, vol. 96, No. 4, Apr. 2005, pp. 206-211.

Widschwendter et al.: "Analysis Of Aberrant DNA Methylation and Human Papillomavirus DNA in Cervicovaginal Specimens To Detect Invasive Cervical Cancer and Its Precursors" Clinical Cancer Research, The American Association for Cancer Research, US, vol. 10, No. 10, May 15, 2004, pp. 3396-3400.

Yanagi et al., "Hepatitis C Virus: An Infectious Molecular Clone of a Second Major Genotype (2A) and Lack of Viability of Intertypic 1A and 2A Chimeras," Virology 262, pp. 250-263 (1999).

Zeschnigk et al., "A novel real-time PCR assay for quantitative analysis of methylated alleles (QAMA): analysis of the retinoblastoma locus," Nucleic Acid Research 2004, vol. 32, No. 16, pp. 1-5.

Bakker et al. JBC, vol. 277, No. 25, pp. 22573-22580, Jun. 2002.
Cameron et al., Blood, vol. 94, No. 7, pp. 2445-2451, Oct. 1999.
Cohen, Y. et al, "Hypermethylation of CpG Island Loci of Multiple Tumor Suppressor Genes in Retinoblastoma", Experimental Eye Research, 2008, vol. 86, No. 2, pp. 201-206.

Cottrell et al., A real-time PCR assay for DNA-methylation-specific blockers. Nucleic Acid Research, 32(1):e10 (8 pages). Jan. 13, 2004.

Esteller et al., Cancer Research, vol. 58, pp. 4514-4518, Oct. 1998.

Hitchcock, T.M. et al., "Cleavage of deoxyoxanosine-containing oligodeoxyribonucleotides by bacterial endonuclease V", Nucleic Acids Research, 2004, vol. 32, No. 13, pp. 4071-4080.

International Search Report issued in corresponding PCT Application No. PCT/AU2008/001891, mailed Feb. 3, 2009.

International Search report issued in PCT Application No. PCT/AU2008/001751, mailed Feb. 18, 2009.

International Search report issued in PCT Application No. PCT/AU2008/001796, mailed Feb. 23, 2009.

Lee et al., Cancer Epidemiology, Biomarkers, Prevention, vol. 6, pp. 443-450, Jun. 1997.

Longo, M.C. et al., "Use of Uracil DNA Glycosylase to Control Carry-Over Contamination in Polymerase Chain Reactions", Gene, vol. 93, No. I, pp. 125-128, Sep. 1990.

Melki et al., Cancer Research, vol. 59, pp. 3730-3740, Aug. 1999.

Munson, K. et al. Recovery of bisulphite-converted genomic sequences in the methylation-sensitive QPCR. Nucleic Acids Research (2007) vol. 35, No. 9, pp. 2893-2903.

Notice of Allowance issued in U.S. Appl. No. 10/561,029 dated May 28, 2010.

Notice of Allowance issued in U.S. Appl. No. 11/575,060, mailed Jun. 15, 2010.

Notice of Allowance issued in U.S. Appl. No. 11/573,873, mailed Jul. 1, 2010.

Office Action in U.S. Appl. No. 10/561,029 dated Apr. 13, 2009.

Office Action in U.S. Appl. No. 11/573,873 dated Mar. 23, 2010.

Office Action in U.S. Appl. No. 11/573,873 dated Sep. 2, 2009.

Office Action in U.S. Appl. No. 11/660,586 dated Apr. 15, 2010.

Office Action in U.S. Appl. No. 11/756,534 dated Aug. 10, 2009.

Office Action in U.S. Appl. No. 11/756,534 dated Jun. 8, 2010.

Office Action in U.S. Appl. No. 12/066,644 dated Apr. 22, 2010.

Pao et al., Human Molecular Genetics, vol. 10, No. 9, pp. 903-910, 2001.

Ratushna V.G. et al.: "Secondary structure in the target as a confounding factor in synthetic oligomer microarray design," BMC Genomics, vol. 6, No. 1, Mar. 2005, p. 31.

Shao-Qing, Chinese Journal of Agricultural Biotechnology, vol. 4, No. 1, pp. 75-79, 2007.

Shibutani, S. et al, "Translesional Synthesis on DNA Templates Containing a Single Abasic Site", The Journal of Biological Chemistry, 1997; vol. 272, No. 21, pp. 13916-13922.

Shiraishi, M. et al. "High Speed Conversion of Cytosine to Uracil in Bisulphite Genomic Sequencing Analysis of DNA Methylation;" DNA Research (2004) vol. II, pp. 409-415.

Strategene, 1988 Catalog, p. 39.

Toyota et al., Cancer Research, vol. 59, pp. 4535-4541, Sep. 1999.

Triplett, J. W. et al., Carbon-13 NMR Investigation of the Bisulphite Induced Changes in Yeast RNA; Biochemical and Biophysical Research Communications (1977), vol. 77, No. 4, pp. 1170-1175.

Tsuda et al., *Gynecologic Oncology*, vol. 91, pp. 476-485, 2003.

Verma M: "Viral genes and methylation" Annals of the New York Academy of Sciences 200303 US, vol. 983, Mar. 2003, pp. 170-180.

Virmani et al., Clinical Cancer Research, vol. 7, No. 3, pp. 584-489, Mar. 2001.

Yao, M. et al, "Further Characterization of *Escherichia coli* Endonuclease V", Journal of Biological Chemistry, 1997, vol. 272, No. 49, pp. 30774-30779.

Christensen et al., "Intercalating nucleic acids containing insertions of 1-o-(1-pyrenylmethyl)glycerol: stabilization of dsDNA and discrimination of DNA over RNA." Nucleic Acid Res. vol. 30, No. 22, pp. 4918-4925, (2002).

Clark et al., "High sensitivity mapping methylated cytosines." Nucleic Acids Research, 22(15): 2990-2997 (1994).

Clark, et al., "Bisulphite genomic sequencing of methylated cytosines." Laboratory Methods for the Detection of Mutations and Polymorphisms in DNA. Graham R. Taylor, Ed. CRC Press, New York (1997), pp. 151-162.

NCBI Database Accession No. M24485, Dec. 5, 1994.

Dean et al., "Comprehensive human genome amplification using multiple displacement amplification." PNAS, 99(8): 5261-5266 (2002).

Eads et al., "MethyLight: a high-throughput assay to measure DNA methylation." Nucleic Acids Research, 28(8):e32 i-viii (2000).

Feil, et al., "Methylation analysis on individual chromosomes: improved protocol for bisulphite genomic sequencing." (1994) Nucleic Acids Research 22(4): 695-696.

Frommer et al., "A genomic sequencing protocol that yields a positive display of 5-methylcytosine residues in individual DNA strands," Proc. Natl. Acad. Sci. 89: 1827-1831 (1992).

Grigoriev et al., "A Triple Helix-forming Oligonucleotide-Intercalator Conjugate Acts as a Transcriptional Repressor via Inhibition of NFkB Binding to Interleukin-2 Receptor a-Regulatory Sequence." The Journal of Biological Chemistry, 267 (5): 3389-3395 (1992).

Grunau, et al., "Bisulfite genomic sequencing: systematic investigation of critical experimental parameters." Nucleic Acid Research, (2001) vol. 29, No. 13e65, pp. 1-7.

Hakelien et al., "Reprogramming fibroblasts to express T-cell functions using cell extracts." Nature Briotechnology, 20(5): 460-466 (2002).

Hakelien et al., "Novel Approaches to Transdifferentation", Cloning and Stem Cells, 4: 379-387 (2002).

Herman, et al., "Methylation-specific PCR: a novel PCR assay for methylation status of CpG islands." (1996) Proc. Natl. Acad. Sci. 93:9821-9826.

Hosono et al. "Unbiased Whole-Genome Amplification Directly from Clinical Samples." *Genome Research*; 13:954-964 (2003).

International Human Genome Sequencing Consortium, "Initial sequencing and analysis of the human genome," Nature, 409(6822): 860-921 (2001).

International Preliminary Report on Patentability issued on the corresponding PCT Application No. PCT/AU2006/000698, dated Apr. 20, 2007.

International Search Report Issued on the corresponding PCT Application No. PCT/AU2006/000698, dated Aug. 1, 2006.

Kinoshita et al., "Methylation of the androgen receptor minimal promoter silences transcription in human prostate cancer." Cancer Research, 60(13): 3623-3630 (Jul. 1, 2000).

Kono, "Nuclear transfer and reprogramming." Reviews of Reproduction, vol. 2 No. 2, pp. 74-80 (May 1997).

Millar et al., "A distinct sequence (ATAAA)n separates methylated and unmethylated domains at the 5'-end of the GSTPI CpG island," J. Biol. Chem., 275(32): 24893-24899 (2000).

Millar et al., "Detailed methylation analysis of the glutathione S-transferase pi (GSTPI) gene in prostate cancer," Oncogene 18(6): 1313-1324, (1999).

Monk, " Epigentic programming of differential gene expression in development and evolution" Dev. Genetics, vol. 17, pp. 183-197 (1995).

Newton et al., "The production of PCR products with 5' single-stranded tails using primers that incorporate novel phosphoramidite intermediates." Nucleic Acid Res. vol. 21 No. 5, pp. 1155-1162 (1993).

Office Action in U.S. Appl. No. 10/416,637 dated May 4, 2006.

Office Action in U.S. Appl. No. 10/428,310 dated Aug. 31, 2006.

Office Action in U.S. Appl. No. 10/428,310 dated Jan. 4, 2006.

Office Action in U.S. Appl. No. 10/428,310 dated Jul. 5, 2006.

Office Action in U.S. Appl. No. 10/428,310 dated Nov. 3, 2006.

Office Action in U.S. Appl. No. 10/536,633 dated Apr. 4, 2007.

Office Action in U.S. Appl. No. 10/536,633 dated Jan. 25, 2007.

Okada, et al., "Sequence Determination of Rat U5 RNA Using a Chemical Modification Procedure for Counteracting Sequence Compression." (1982) J. Biochem. 91: 1281-1291.

Olek, et al. "A modified and improved method for bisulphate based cytosine methylation analysis." (1996) Nucleic Acids Research, 24(24): 2065-5066.

Paulin et al., "Urea improves efficiency of bisulphite-mediated sequencing of 5'-methylcytosine in genomic DNA." Nucleic Acid Research, 26(21): 5009-5010 (Nov. 1, 1998).

Pietrobono et al., "Quantitative analysis of DNA demethylation and transcriptional reactivation of the FMR1 gene in fragile X cellstreated with 5-azadeoxycytidine." Nucleic Acids Research, 30(14): 3278-3285 (2002).

Raizis et al., "A Bisulfite method of 5-Methylcytosine mapping that minimizes template degradation", Anal. Biochem., 226: 161-166 (1995).

Rein et al., "Identifying 5-methylcytosine and related modifications in DNA genomes." Nucleic Acids Research, 26 (10): 2255-2264 (May 15,1998).

Robertson et al., "Methylation of the Epstein-Barr virus genome in normal Lymphocytes", Blood, 90: 4480-4484 (1997).

Robertson et al. "DNA methylation: past, present, and future directions." Carcinogenesis. 21(3): 461-467 (2000).

Sakaguchi et al. "Cautionary Note on the Use of dUMP-Containing PCR Primers with *Pfu* and VentR® DNA Polymerases." *Biotechniques*; 21(3):368 & 370 (1996).

Sakashita et al., "Dynamic DNA methylation change in the CpG island region of p15 during human myeloid development", J. Clin. Invest., 108: 1195-1204 (2001).

Shapiro et al., "Deamination of cytosine derivatives by bisulfite. Mechanism of the reaction," J. Am. Chem. Soc., 96: 906-912 (1974).

Specification and Preliminary Amendment from co-pending U.S. Appl. No. 10/555,465, filed Aug. 28, 2006.

Tada et al., "Embryonic germ cells induce epigenetic reprogramming of somatic nucleus in hybrid cells." The EMBO Journal, 16(21): 6510-6520 (1997).

Telenius et al. "Degenerate Oligonucleotide-Primed PCR: General Amplification of Target DNA by a Single Degenerate Primer." *Genomics*; 13(3):718-725 (1992).

Tohgi et al., "Decrease with age in methylcytosines in the promoter region of receptor for advanced glycated end products (RAGE) gene in autopsy human cortex", Molecular Brain Research, 65:124-128 (1999).

Venter et al., "The sequence of the human genome," Science, 292 (5523): 1304-1351, 2001.

Waranecke et al., "Detection and measurement of PCR bias in quantitative methylation analysis of bisulphite-treated DNA," Nucleic Acids Research, vol. 25 No. 21, pp. 4422-4426, (1997).

Xiong et al., "COBRA: a sensititive and quantitative DNA methylation assay." (1997) Nucleic Acids Research, 25 (12): 2532-2534.

Nilsson et al. *Science*. 265:2085-2088 (1994).

\* cited by examiner

Figure 1A. 5 Units of Ligase enzyme
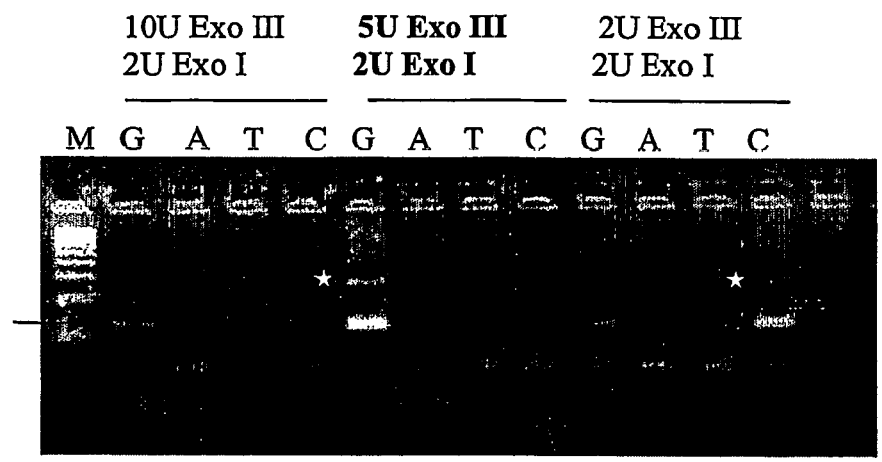
Figure 1B. 10 Units of Ligase enzyme
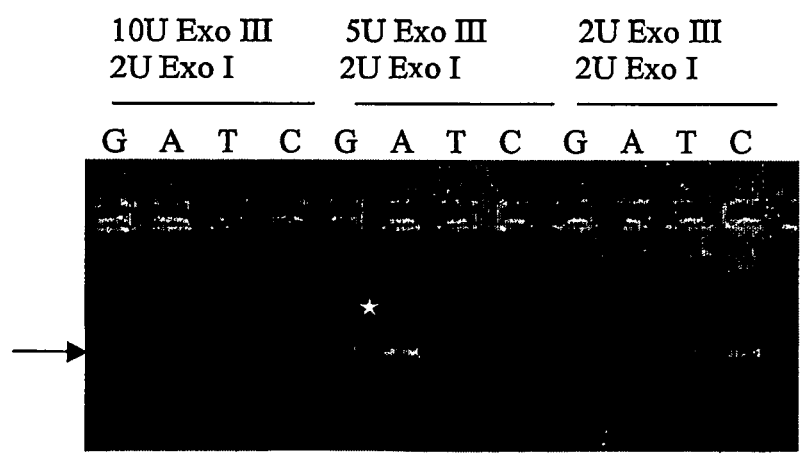

Figure 3
Panel A High concentration DNA
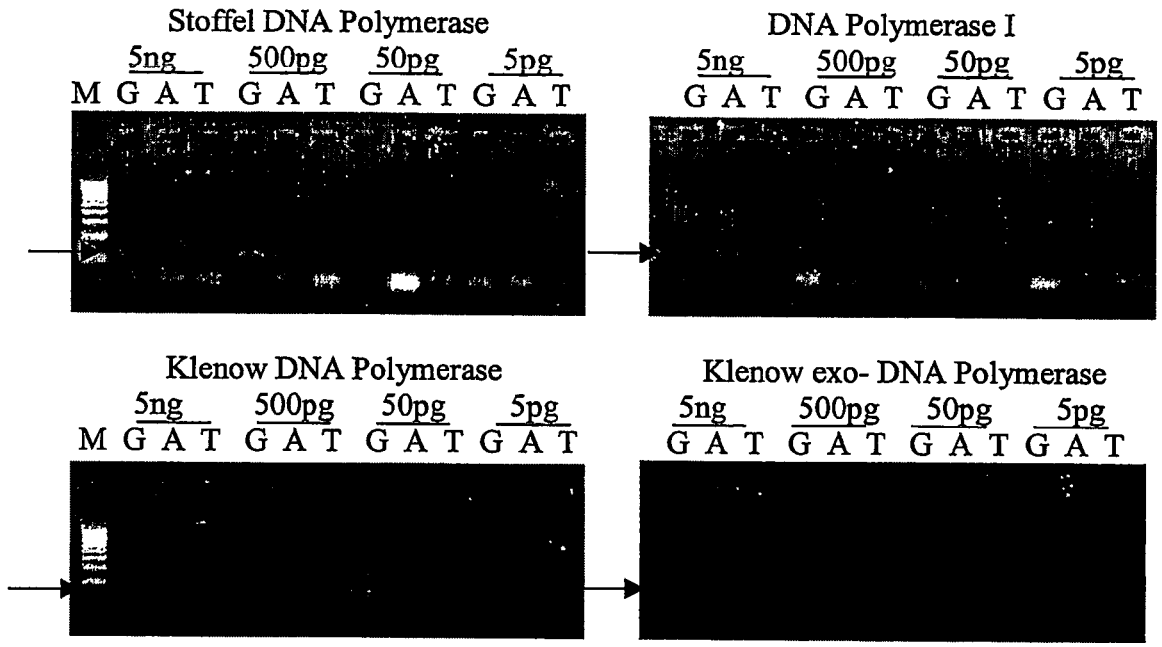
Panel B Low concentration DNA
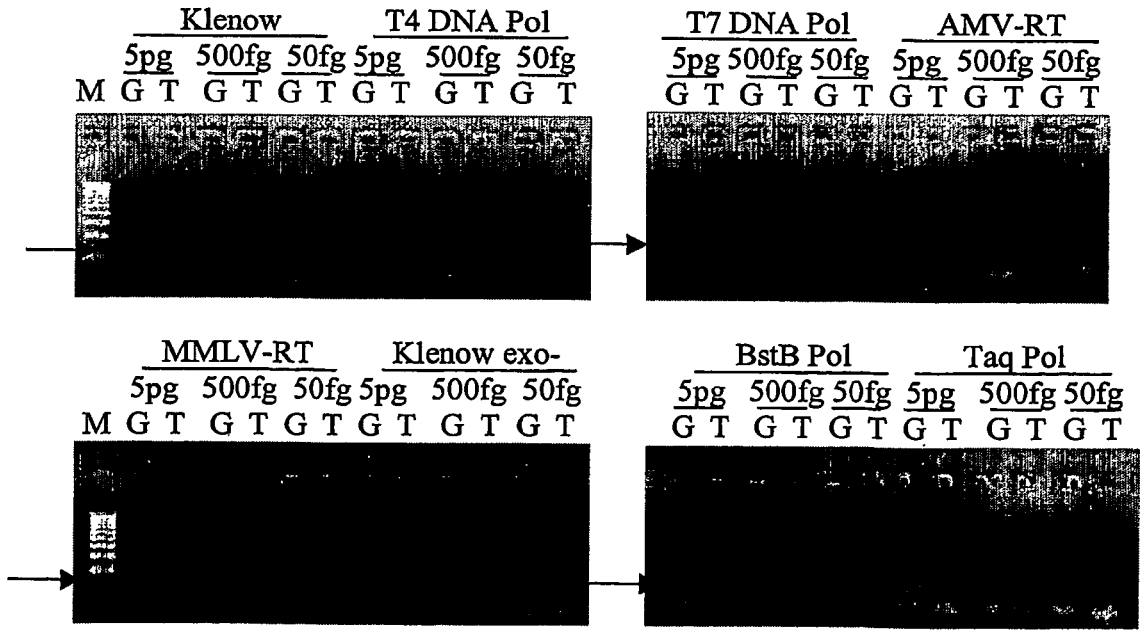

1. 5 ng DNA
2. 500 pg DNA
3. 50 pg DNA
4. 5 pg DNA
5. 500 fg DNA
6. 50 fg DNA

Figure 8

Example #1

Methylated DNA sequence

Top strand wild type genomic     5'-AGA AAA GAC ATC TGG C GG AAA CCT CGC C-3'
Top strand bisulphite converted   5'-AGA AAA GAT ATT TGG C GG AAA TTT YGT T-3'
               Clamp#1   TCT TTT CTA TAA ACC G  CC TTT AAA RCA A
Clamp#2

Example #2

Unmethylated DNA sequence

Top strand wild type genomic     5'-AGA AAA GAC ATC TGG C GG AAA CCT CGC C-3'
Top strand bisulphite converted   5'-AGA AAA GAT ATT TGG T GG AAA TTT YGT T-3'
               Clamp#1   TCT TTT CTA TAA ACC A  CC TTT AAA RCA A
Clamp#2

Figure 9

Example#3

Methylated DNA sequence

Top strand wild type genomic     5'-AGA AAA GAC ATC TGG C GG AAA CCT CGC C-3'
Top strand bisulphite converted   5'-AGA AAA GAT ATT TGG C GG AAA TTT YGT T-3'
               Clamp#1   TCT TTT CTA TAA ACC    CC TTT AAA RCA A  Clamp#2

Example#4

Unmethylated DNA sequence

Top strand wild type genomic     5'-AGA AAA GAC ATC TGG C GG AAA CCT CGC C-3'
Top strand bisulphite converted   5'-AGA AAA GAT ATT TGG T GG AAA TTT YGT T-3'
               Clamp#1   TCT TTT CTA TAA ACC    CC TTT AAA RCA A  Clamp#2

Figure 10

Example #5

Methylated DNA sequence

Top strand wild type genomic    5'-AGA AAA GAC ATC TGG C GG AAA CCT CGC C-3'
Top strand bisulphite converted    5'-AGA AAA GAT ATT TGG C GG AAA TTT YGT T-3'
                                        -TCT TTT CTA TAA ACC G CC TTT AAA RCA A
                                                                                     Clamp#2
           Clamp#1
                                                                                       Clamp#3
                                          AAA AAA AAC ATC TAA CG A AAA CCT ATA CRC C
Bottom strand bisulphite covverted  3'-TTT TTT TTG TAG ATT G C T TTT GGA TAT GYG G-5'
Bottom strand wild type genomic    3'-TCT TTT CTG TAG ACC G C T TTT GGA CAC GCG G-5'

Example #6

Unmethylated DNA sequence

Top strand wild type genomic    5'-AGA AAA GAC ATC TGG C GG AAA CCT CGC C-3'
Top strand bisulphite converted    5'-AGA AAA GAT ATT TGG T GG AAA TTT YGT T-3'
                                        -TCT TTT CTA TAA ACC A CC TTT AAA RCA A
                                                                                     Clamp#2
           Clamp#1
                                                                                      Clamp#3
                                          AAA AAA AAC ATC TAAC A A AAA CCT ATA CRC C
Bottom strand bisulphite covverted  3'-TTT TTT TTG TAG ATT G T T TTT GGA TAT GYG G-5'
Bottom strand wild type genomic    3'-TCT TTT CTG TAG ACC G C T TTT GGA CAC GCG G-5'

Figure 11

Example #7

Methylated DNA sequence

Top strand wild type genomic        5'-AGA AAA GAC ATC TGG C GG AAA CCT CGC C-3'
Top strand bisulphite converted     5'-AGA AAA GAT ATT TGG C GG AAA TTT YGT T-3'
                                    ⌐TCT TTT CTA TAA ACC    CC TTT AAA RCA A
                                                                        Clamp#2
        Clamp#1
                                                                        Clamp#3
                                    ⌐AAA AAA AAC ATC TAA C  A AAA CCT ATA CRC C
Bottom strand bisulphite covverted  3'-TTT TTT TTG TAG ATT G C T TTT GGA TAT GYG G-5'
Bottom strand wild type genomic     3'-TCT TTT CTG TAG ACC G C T TTT GGA CAC GCG G-5'

Example #8

Unmethylated DNA sequence

Top strand wild type genomic        5'-AGA AAA GAC ATC TGG C GG AAA CCT CGC C-3'
Top strand bisulphite converted     5'-AGA AAA GAT ATT TGG T GG AAA TTT YGT T-3'
                                    ⌐TCT TTT CTA TAA ACC A CC TTT AAA RCA A
                                                                        Clamp#2
        Clamp#1
                                                                        Clamp#3
                                    ⌐AAA AAA AAC ATC TAAC A A AAA CCT ATA CRC C
Bottom strand bisulphite covverted  3'-TTT TTT TTG TAG ATT G T T TTT GGA TAT GYG G-5'
Bottom strand wild type genomic     3'-TCT TTT CTG TAG ACC G C T TTT GGA CAC GCG G-5'

Figure 12

Example #9

Methylated DNA sequence

Top strand wild type genomic 5'-AGA AAA GAC ATC TGG C GG AAA CCT CGC C-3'
Top strand bisulphite converted 5'-AGA AAA GAT ATT TGG C GG AAA TTT YGT T-3'
                      TCT TTT CTA TAA ACC G CC TTT AAA RCA A Clamp#1                                                         Clamp#2

AAA AAA AAC ATC TAA CG A AAA CCT ATA CRC C
Bottom strand bisulphite covverted 3'-TTT TTT TTG TAG ATT G C T TTT GGA TAT GYG G-5'
Bottom strand wild type genomic 3'-TCT TTT CTG TAG ACC G C T TTT GGA CAC GCG G-5'

Example #10

Unmethylated DNA sequence

Top strand wild type genomic 5'-AGA AAA GAC ATC TGG C GG AAA CCT CGC C-3'
Top strand bisulphite converted 5'-AGA AAA GAT ATT TGG T GG AAA TTT YGT T-3'
                      TCT TTT CTA TAA ACC A CC TTT AAA RCA A Clamp#1                                                         Clamp#2

AAA AAA AAC ATC TAAC A A AAA CCT ATA CRC C
Bottom strand bisulphite covverted 3'-TTT TTT TTG TAG ATT G T T TTT GGA TAT GYG G-5'
Bottom strand wild type genomic 3'-TCT TTT CTG TAG ACC G C T TTT GGA CAC GCG G-5'

Figure 13

Example#11

Methylated DNA sequence

Top strand wild type genomic    5'-AGA AAA GAC ATC TGG C GG AAA CCT CGC C-3'
Top strand bisulphite converted    5'-AGA AAA GAT ATT TGG C GG AAA TTT YGT T-3'

⌒TCT TTT CTA TAA ACC    CC TTT AAA RCA A⌒

Clamp#1                                                                                      Clamp#2

⌣AAA AAA AAC ATC TAA C   A AAA CCT ATA CRC C⌣

Bottom strand bisulphite covverted  3'-TTT TTT TTG TAG ATT G C T TTT GGA TAT GYG G-5'
Bottom strand wild type genomic    3'-TCT TTT CTG TAG ACC G C T TTT GGA CAC GCG G-5'

Example#12

Unmethylated DNA sequence

Top strand wild type genomic    5'-AGA AAA GAC ATC TGG C GG AAA CCT CGC C-3'
Top strand bisulphite converted    5'-AGA AAA GAT ATT TGG T GG AAA TTT YGT T-3'

⌒TCT TTT CTA TAA ACC    CC TTT AAA RCA A⌒

Clamp#1                                                                                      Clamp#2

⌣AAA AAA AAC ATC TAAC   A AAA CCT ATA CRC C⌣

Bottom strand bisulphite covverted  3'-TTT TTT TTG TAG ATT G T T TTT GGA TAT GYG G-5'
Bottom strand wild type genomic    3'-TCT TTT CTG TAG ACC G C T TTT GGA CAC GCG G-5'

Gene #1

Add polymerase and ligase

| Zip-1 | Clamp A |
| Zip-2 | Clamp B |
| Zip-3 | Clamp C |
| Zip-4 | Clamp D |
| Zip-5 | Clamp E |

NUCLEIC ACID DETECTION ASSAY

CROSS-REFERENCE TO RELATED APPLICATIONS

This application is the U.S. National Phase filing under 35 U.S.C. §371 of PCT/AU2004/001196, filed Sep. 3, 2004, which designated the United States and was published in English on Mar. 17, 2005, which claims priority under 35 U.S.C. §119(a) to Australian Patent Application No. 2003904832, filed Sep. 4, 2003.

TECHNICAL FIELD

The invention relates to nucleic acid detection assays and in particular to improved oligonucleotide assays using a bisulphite clamp. The invention also relates to methods for distinguishing specific base sequences including 5-methyl cytosine bases in nucleic acids using these assays.

BACKGROUND ART

A number of procedures are presently available for the detection of specific nucleic acid molecules. These procedures typically depend on sequence-dependent hybridisation between the target nucleic acid and nucleic acid probes which may range in length from short oligonucleotides (20 bases or less) to sequences of many kilobases (kb).

The most widely used method for amplification of specific sequences from within a population of nucleic acid sequences is that of polymerase chain reaction (PCR) (Dieffenbach C and Dveksler G eds. PCR Primer: A Laboratory Manual. Cold Spring Harbor Press, Plainview N.Y.). In this amplification method, oligonucleotides, generally 15 to 30 nucleotides in length on complementary strands and at either end of the region to be amplified, are used to prime DNA synthesis on denatured single-stranded DNA. Successive cycles of denaturation, primer hybridisation and DNA strand synthesis using thermostable DNA polymerases allows exponential amplification of the sequences between the primers. RNA sequences can be amplified by first copying using reverse transcriptase to produce a cDNA copy. Amplified DNA fragments can be detected by a variety of means including gel electrophoresis, hybridisation with labelled probes, use of tagged primers that allow subsequent identification (eg. by an enzyme linked assay), use of fluorescently-tagged primers that give rise to a signal upon hybridisation with the target DNA (eg. Beacon and TaqMan systems).

As well as PCR, a variety of other techniques have been developed for detection and amplification of specific sequences. One example is the ligase chain reaction (Barany F Genetic disease detection and DNA amplification using cloned thermostable ligase. Proc. Natl. Acad. Sci. USA 88:189-193 (1991)).

For direct detection, the target nucleic acid is most commonly separated on the basis of size by gel electrophoresis and transferred to a solid support prior to hybridisation with a probe complementary to the target sequence (Southern and Northern blotting). The probe may be a natural nucleic acid or analogue such as peptide nucleic acid (PNA) or locked nucleic acid (LNA). The probe may be directly labelled (eg. with $^{32}P$) or an indirect detection procedure may be used. Indirect procedures usually rely on incorporation into the probe of a "tag" such as biotin or digoxigenin and the probe is then detected by means such as enzyme-linked substrate conversion or chemiluminescence.

Another method for direct detection of nucleic acid that has been used widely is "sandwich" hybridisation. In this method, a capture probe is coupled to a solid support and the target nucleic acid, in solution, is hybridised with the bound probe. Unbound target nucleic acid is washed away and the bound nucleic acid is detected using a second probe that hybridises to the target sequences. Detection may use direct or indirect methods as outlined above. The "branched DNA" signal detection system is an example that uses the sandwich hybridization principle (Urdea M S et al. Branched DNA amplification multimers for the sensitive, direct detection of human hepatitis viruses. Nucleic Acids Symp Ser. 1991; (24): 197-200).

A rapidly growing area that uses nucleic acid hybridisation for direct detection of nucleic acid sequences is that of DNA micro-arrays (Young R A Biomedical discovery with DNA arrays. Cell 102: 9-15 (2000); Watson A New tools. A new breed of high tech detectives. Science 289:850-854 (2000)). In this process, individual nucleic acid species, that may range from oligonucleotides to longer sequences such as cDNA clones, are fixed to a solid support in a grid pattern. A tagged or labelled nucleic acid population is then hybridised with the array and the level of hybridisation with each spot in the array quantified. Most commonly, radioactively- or fluorescently-labelled nucleic acids (eg. cDNAs) were used for hybridisation, though other detection systems were employed.

One problem associated with the use of micro-arrays for genomic typing analysis is that before individual sites can be analysed they usually have to be pre-amplified in some way. Most methods rely on PCR amplification of the target sequence. However, when the number of primer sets in the reaction mix is n target sequences, any $2n^2+n$ possible pair-wise combination of probes may give rise to non-specific amplification products (Landegren and Nilsson. Locked on target: strategies for future gene diagnostics. Ann. Med. 1997; (29): 585-590). To address this technique, padlock probes have been developed. With these probes, non-specific reactions create linearised molecules whereas specific hybridization events lead to dimeric molecules which can be distinguished from the linearised molecules by the use of exonucleases (Nilsson et al. Padlock probes: circularised oligonucleotides for local DNA detection. 1994; Science 92650; 2085-2088). However, for the specific detection of genomic variations typically four probes would be used for the detection of each individual polymorphic site leading to a very large number of probes to be generated for whole genome scanning.

Another recent technique, molecular inversion probes (MIP) has been demonstrated to produce a high level of multiplexing in a single tube. It has been reported that more that 1000 probes can be multiplexed in a single tube (Hardenbol et al Nature Biotechnology, 21: 673-678). However, both the padlock probe and MIP method require the synthesis of very long oligonucleotides >110 bp which cannot be achieved with most commercial distributors.

Currently, the method of choice to detect methylation changes in DNA, such as were found in the GSTP1 gene promoter in prostate cancer, are dependent on PCR amplification of such sequences after bisulphite modification of DNA. In bisulphite-treated DNA, cytosines are converted to uracils (and hence amplified as thymines during PCR) while methylated cytosines are non-reactive and remain as cytosines (Frommer M, McDonald L E, Millar D S, Collis C M, Watt F, Grigg G W, Molloy P L and Paul C L. A genomic sequencing protocol which yields a positive display of 5-methyl cytosine residues in individual DNA strands. PNAS 89:

1827-1831 (1992); Clark S J, Harrison J, Paul C L and Frommer M. High sensitivity mapping of methylated cytosines. Nucleic Acids Res. 22: 2990-2997 (1994)). Thus, after bisulphite treatment, DNA containing 5-methyl cytosine bases will be different in sequence from the corresponding unmethylated DNA. Primers may be chosen to amplify non-selectively a region of the genome of interest to determine its methylation status, or may be designed to selectively amplify sequences in which particular cytosines were methylated (Herman J G, Graff J R, Myohanen S, Nelkin B D and Baylin S B. Methylation-specific PCR: a novel PCR assay for methylation status of CpG islands. PNAS 93:9821-9826 (1996)).

Alternative methods for detection of cytosine methylation include digestion with restriction enzymes whose cutting is blocked by site-specific DNA methylation, followed by Southern blotting and hybridisation probing for the region of interest. This approach is limited to circumstances where a significant proportion (generally >10%) of the DNA is methylated at the site and where there is sufficient DNA, about 1 to 5 µg, to allow for detection. Digestion with restriction enzymes whose cutting is blocked by site-specific DNA methylation is followed by PCR amplification using primers that flank the restriction enzyme site(s). This method can utilise smaller amounts of DNA but any lack of complete enzyme digestion for reasons other than DNA methylation can lead to false positive signals.

The present inventors have now developed methods utilizing oligonucleotide clamps for the sensitive and specific detection of methylated nucleic acids which greatly reduce the problems associated with non-specific amplification of non-target sequences and increases the levels of multiplexing which can be carried out in an individual reaction tube. This makes the technique ideal for whole genome analysis of methylation patterns and also amenable to robotic manipulation.

DISCLOSURE OF INVENTION

In a first aspect, the present invention provides a method for determining the methylation status of a potential methylation site in genomic nucleic acid comprising:
(a) treating genomic nucleic acid with an agent which modifies cytosine bases but does not modify 5methyl-cytosine bases under conditions to form a modified nucleic acid template containing a potential methylation site;
(b) providing a first clamp containing a first capture sequence complementary to a region flanking one side of the potential methylation site in the modified nucleic acid template;
(c) providing a second clamp containing a second capture sequence complementary to a region flanking the other side of the potential methylation site in the modified nucleic acid template;
(d) allowing the first clamp and the second clamp to hybridise to the modified nucleic acid template;
(e) ligating the hybridised first and second clamps to form a probe spanning the potential methylation site in the modified nucleic acid template;
(f) digesting the modified nucleic acid template; and
(g) detecting the probe and determining the methylation status of the potential methylation site in the modified genomic nucleic acid.

In a second aspect, the present invention provides a method for determining the methylation status of a potential methylation site in genomic nucleic acid comprising:
(a) treating genomic nucleic acid with an agent which modifies cytosine bases but does not modify 5-methyl-cytosine bases under conditions to form a modified nucleic acid template;
(b) providing a first clamp containing a first capture sequence complementary to a region flanking one side of the potential methylation site in the modified nucleic acid template;
(c) providing a second clamp containing a second capture sequence complementary to a region flanking the other side of the potential methylation site in the modified nucleic acid template;
(d) allowing the first clamp and the second clamp to hybridise to the modified nucleic acid template such that there is no complementary base(s) at the potential methylation site;
(e) causing a base or bases to be inserted between the first clamp and the second clamp;
(e) ligating the hybridised clamps to form a probe spanning the potential methylation site in the modified nucleic acid template;
(f) digesting the modified nucleic acid template; and
(g) detecting the probe and determining the methylation status of the potential methylation site in the modified genomic nucleic acid.

In a third aspect, the present invention provides a method for determining the methylation status of a potential methylation site on genomic nucleic acid comprising:
(a) treating genomic nucleic acid with an agent which modifies cytosine bases but does not modify 5-methyl-cytosine bases under conditions to form a modified nucleic acid template containing two complementary strands of nucleic acid containing a potential methylation site;
(b) providing a first clamp containing a first capture sequence and a second capture sequence, first capture sequence being complementary to a region flanking one side of the potential methylation site in the first strand of the modified nucleic acid template, and the second capture sequence being complementary to a region flanking one side of the potential methylation site in the second strand of the modified nucleic acid template;
(c) providing a second clamp containing a third capture sequence complementary to a region flanking the other side the potential methylation site in the first strand of the modified nucleic acid template;
(d) providing a third clamp containing a fourth capture sequence complementary to a region flanking the other side of the potential methylation site in the second strand of the modified nucleic acid template;
(e) allowing the first, second and third clamps to hybridise to the modified nucleic acid template;
(f) ligating the hybridised clamps to form a probe spanning the potential methylation site in the two strands of the modified nucleic acid template;
(g) digesting the modified nucleic acid template; and
(h) detecting the probe and determining the methylation status of the potential methylation sites in the modified genomic nucleic acid.

In a fourth aspect, the present invention provides a method for determining the methylation status of a potential methylation site on genomic nucleic acid comprising:
(a) treating genomic nucleic acid with an agent which modifies cytosine bases but does not modify 5methyl-cytosine bases under conditions to form a modified-nucleic acid template containing two complementary strands of nucleic acid containing a potential methylation site;
(b) providing a first clamp containing a first capture sequence and a second capture sequence, the first capture sequence being complementary to a region flanking one side of the potential methylation site in the first strand of the modified nucleic acid template, and the second capture sequence being complementary to a region flanking one side of the potential methylation site in the second strand of the modified nucleic acid template;

(c) providing a second clamp containing a third capture sequence complementary to a region flanking the other side the potential methylation site in the first strand of the modified nucleic acid template;

(d) providing a third clamp containing a fourth capture sequence complementary to a region flanking the other side of the potential methylation site in the second strand of the modified nucleic acid template;

(e) allowing the first, second and third clamps to hybridise to the modified nucleic acid template such that there is no complementary base at the potential methylation site of at least one of the complementary strands of the modified nucleic acid template;

(f) causing at least one base to be inserted between the first clamp and the second clamp;

(g) ligating the hybridised clamps to form a linear probe spanning the potential methylation site in the two strands of the modified nucleic acid template;

(h) digesting the modified nucleic acid template; and (h) detecting the linear probe and determining the methylation status of the potential methylation sites in the modified genomic nucleic acid.

In a fifth aspect, the present invention provides a method for determining the methylation status of a potential methylation site on genomic nucleic acid comprising:

(a) treating genomic nucleic acid with an agent which modifies cytosine bases but does not modify 5methyl-cytosine bases under conditions to form a modified nucleic acid template containing two complementary strands of nucleic acid containing a potential methylation site;

(b) providing a first clamp containing a first capture sequence and a second capture sequence, first capture sequence being complementary to a region flanking one side of the potential methylation site in the first strand of the modified nucleic acid template and the second capture sequence being complementary to a region flanking one side of the potential methylation site in the second strand of the modified nucleic acid template;

(c) providing a second clamp containing a third capture sequence and a fourth capture sequence, the third capture sequence being complementary to a region flanking the other side the potential methylation site in the first strand of the modified nucleic acid template, and the fourth capture sequence being complementary to a region flanking the other side of the potential methylation site in the second strand of the modified nucleic acid template;

(d) allowing the first clamp and the second clamp to hybridise to the two strands of the modified nucleic acid template;

(e) ligating the hybridised clamps to form a circular probe spanning the potential methylation site in the two strands of the modified nucleic acid template;

(f) digesting the modified nucleic acid template; and (g) detecting the circular probe and determining the methylation status of the potential methylation site in the modified genomic nucleic acid.

In a sixth aspect, the present invention provides a method for determining the methylation status of a potential methylation site on genomic nucleic acid comprising:

(a) treating genomic nucleic acid with an agent which modifies cytosine bases but does not modify 5methyl-cytosine bases under conditions to form a modified nucleic acid template containing two complementary strands of nucleic acid containing a potential methylation site;

(b) providing a first clamp containing a first capture sequence and a second capture sequence, the first capture sequence being complementary to a region flanking one side of the potential methylation site in the first strand of the modified nucleic acid template, and the second capture sequence being complementary to a region flanking one side of the potential methylation site in the second strand of the modified nucleic acid template;

(c) providing a second clamp containing a third capture sequence and a fourth capture sequence, the third capture sequence being complementary to a region flanking the other side the potential methylation site in the first strand of the modified nucleic acid template, and the fourth capture sequence complementary to a region flanking the other side of the potential methylation site in the second strand of the modified nucleic acid template;

(d) allowing the first clamp and the second clamp to hybridise to the two strands of the modified nucleic acid template such that there is no complementary base at the potential methylation site of at least one of the complementary strands of the modified nucleic acid template;

(e) causing at least one base to be inserted between the first clamp and the second clamp;

(f) ligating the hybridised clamps to form a circular probe spanning the potential methylation site in the two strands of the modified nucleic acid template;

(g) digesting the modified nucleic acid template; and (h) detecting the circular probe and determining the methylation status of the potential methylation site in the modified genomic nucleic acid.

The genomic nucleic acid can be DNA or RNA. Preferably, the genomic nucleic acid is DNA.

Preferably, the potential methylation site is cytosine (C) flanked 5' by a guanine (G), termed in the art as CpG doublet.

The modifying agent is preferably selected from bisulfite, acetate or citrate. More preferably, the agent is sodium bisulfite, a reagent, which in the presence of water, modifies cytosine into uracil.

Sodium bisulfite ($NaHSO_3$) reacts readily with the 5,6-double bond of cytosine to form a sulfonated cytosine reaction intermediate which is susceptible to deamination, and in the presence of water gives rise to a uracil sulfite. If necessary, the sulfite group can be removed under mild alkaline conditions, resulting in the formation of uracil. Thus, potentially all cytosines will be converted to uracils. Any methylated cytosines, however, cannot be converted by the modifying reagent due to protection by methylation.

In one preferred form, at least one of the first, second or third clamps contains a universal primer which allows amplification of the probe after the ligation step.

In another preferred form, at least one of the first, second or third clamps contains a capture site which allows capture of the probe.

In another preferred form, at least one of the first, second or third clamps contains a cleavable site. Preferably, the cleavable site is nuclease restriction site or a uracil base.

In one preferred form, the complementary sequence(s) of the first or second clamps spans the potential methylation site.

In another preferred form, the complementary sequence(s) of the first, second or third clamps does not span the potential methylation site.

The clamps are preferably ligated by the use of a suitable enzyme capable of ligating single stranded DNA. Examples of suitable ligases include, but not limited to, Ampligase (Epicentre various cat#'s), T4 DNA ligase (NEB cat#

M0202), *Thermus aquaticus* DNA ligase (NEB cat# M0208), DNA ligase (*E. coli*, NAD) (NEB cat# M0205. It will be appreciated, however, that other ligases would also be suitable for the present invention.

In the fifth and sixth aspects, the clamps are preferably ligated at or near the first and second capture sequences and at or near the third and fourth capture sequences.

When one or more bases are inserted between the clamps, preferably a DNA polymerase is used. Examples of suitable polymerases include, but not limited to, Taq polymerase Stoffel fragment, Taq polymerase, Advantage DNA polymerase, AmpliTaq, Amplitaq Gold, Titanium Taq polymerase, KlenTaq DNA polymerase, Platinum Taq polymerase, Accuprime Taq polymerase. DNA polymerase1, T4 DNA polymerase, T7 DNA polymerase, Klenow large fragment, Klenow exo- DNA polymerase, BstB polymerase. Or any suitable DNA polymerase. It will be appreciated, however, that other polymerases would also be suitable for the present. In this form, preferably the base insertion reaction is carried out in the presence of a single nucleotide type and each nucleotide type is reacted separately. Thus, the insertion of a particular base will be indicative of the identity of complementary base on the modified DNA template.

Preferably, the modified DNA template is digested by the use of Uracil N DNA Glycosylase (UDG or UNG). As the treated DNA template will contain uracils, it is possible to remove the template by treatment with UDG. It will be appreciated, however, that any other digestion method that does not substantially digest the probe would also be suitable for the present invention. An advantage of removal of the nucleic acid template is that any subsequent amplification of the probe will have much less background and allow more accurate amplification and subsequent detection. Furthermore the removal of the nucleic acid template reduces the amount of artefactual products that may non-specifically form.

Suitable methods to detect the probe and determine the methylation status of the potential methylation site in the modified genomic nucleic acid include, but not limited to, incorporation of the missing base(s) between the first and second clamps, specific amplification of the probe. Numerous possible detection systems exist to determine the epigenetic status of the desired sample. Detection systems include but not limited to:

I. Hybridization of appropriately labelled amplified nucleic acid to a micro-array type device which could select for 10→60,000 individual components. The arrays could be composed of either intercalating nucleic acids (INAs, see WO 03/051901), PNAs or nucleotide or modified nucleotides arrays onto any suitable solid surface such as glass, plastic, mica, nylon, bead, magnetic bead, fluorescent bead or membrane.

II. Southern blot type detection systems.

III. Real-Time PCR quantitation of specific or multiple genomic amplified fragments or any variation such as molecular beacons, scorpions and the like.

IV. Detection systems using fluorescent beads, enzyme conjugates, radioactive beads, etc.

V. Any other amplification system such as ligase chain reaction, etc.

VI. Isothermal nucleic acid amplification technologies such as strand displacement amplification (SDA), rolling circle amplification.

Prior to the present invention, detection of a site of interest in genomic nucleic acid has not been achieved using bisulphite treatment, specific hybridisation of two 'flanking' clamps, optionally base insertion between the clamps, ligation of the two clamps, followed by removal of the template nucleic acid. The treated nucleic acid acts as a scaffold or template for aligning of the first and second clamps and is then removed. In contrast, most prior art assays require capture and the retention of the nucleic acid template.

One advantage of the present invention is that it does not necessarily require amplification of the genomic nucleic acid for the method to be used.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia prior to development of the present invention.

In order that the present invention may be more clearly understood, preferred forms will be described with reference to the following drawings and examples.

BRIEF DESCRIPTION OF THE DRAWINGS

FIG. 1 shows effect of Exonuclease III concentration and Ligase concentration on Clamp specificity (according to sixth aspect).

FIG. 3 shows effect of polymerase on the clamp reaction (according to sixth aspect).

FIG. 8 shows examples of the first aspect of the present invention.

FIG. 9 shows examples of the second aspect of the present invention.

FIG. 10 shows examples of the third aspect of the present invention.

FIG. 11 shows examples of the fourth aspect of the present invention.

FIG. 12 shows examples of the fifth aspect of the present invention.

FIG. 13 shows examples of the sixth aspect of the present invention.

MODE(S) FOR CARRYING OUT THE INVENTION

Materials and Methods

Clamps

Figure 2:
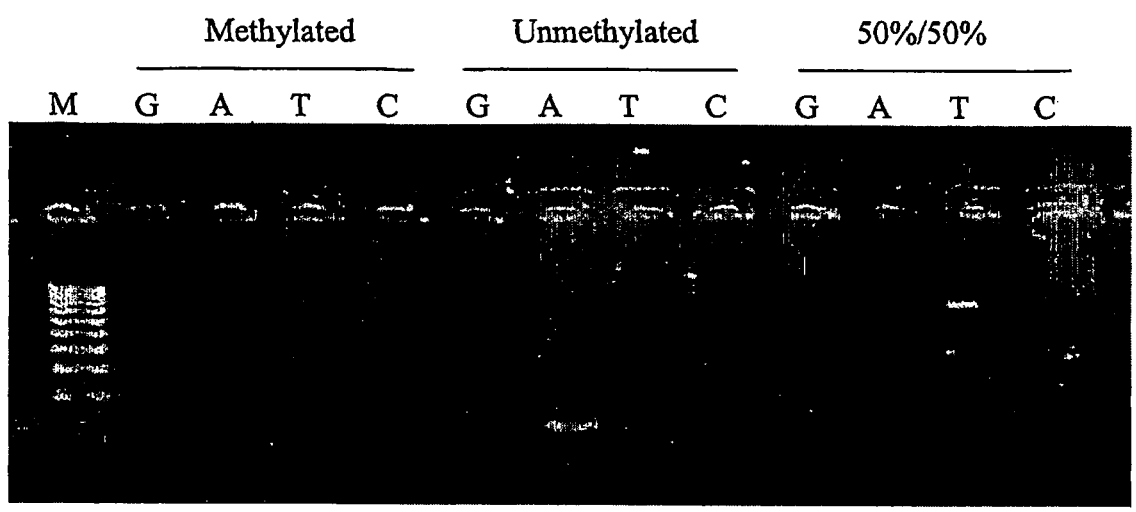
FIG. 2 shows detection of methylated, unmethylated and a mixture of 50% methylated+50% unmethylated DNA (according to sixth aspect).

Each clamp can be an oligonucleotide or oligonucleotide analogue selected from DNA, RNA, locked nucleic acid (LNA), peptide nucleic acid (PNA), MNA, altritol nucleic acid (ANA), hexitol nucleic acid (HNA), intercalating nucleic acid (INA), cyclohexanyl nucleic acid (CNA) and mixtures thereof and hybrids thereof, as well as phosphorous atom modifications thereof, such as but not limited to phosphorothioates, methyl pholates, phosphoramidites, phosphorodithiates, phosphoroselenoates, phosphotriesters and phosphoboranoates. Non-naturally occurring nucleotides include, but not limited to the nucleotides comprised within DNA, RNA, PNA, INA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3,0]amide-DNA, β-D-Ribopyranosyl-NA, α-L-Lyxopyranosyl-NA, 2'-R-RNA, α-L-RNA or α-D-RNA, β-D-RNA. In addition non-phosphorous containing compounds may be used for linking to nucleotides such as but not limited to methyliminomethyl, formacetate, thioformacetate and linking groups comprising amides. In particular nucleic acids and nucleic acid analogues may comprise one or more intercalator pseudonucleotides.

Preferably, the clamps are DNA oligonucleotides.

Genomic Nucleic Acid

Genomic nucleic acid can be DNA or RNA obtained from plants, animals, microorganisms such as bacteria, fungi yeasts and viruses. Preferably, the nucleic acid is DNA, more preferably genomic DNA from an animal or human, or nucleic acid of an infectious agent of animal or human cells.

Bisulphite Treatment of DNA

An exemplary protocol for effective bisulphite treatment of nucleic acid is set out below. The protocol results in retaining substantially all DNA treated. This method is also referred to herein as the Human Genetic Signatures (HGS) method. It will be appreciated that the volumes or amounts of sample or reagents can be varied.

Preferred method for bisulphite treatment can be found in U.S. Ser. No. 10/428,310 or PCT/AU2004/000549 incorporated herein by reference.

To 2 μg of DNA, which can be pre-digested with suitable restriction enzymes if so desired, 2 μl (1/10 volume) of 3 M NaOH (6 g in 50 ml water, freshly made) was added in a final volume of 20 μl. This step denatures the double stranded DNA molecules into a single stranded form, since the bisulphite reagent preferably reacts with single stranded molecules. The mixture was incubated at 37° C. for 15 minutes. Incubation at temperatures above room temperature can be used to improve the efficiency of denaturation.

After the incubation, 208 μl M Sodium Metabisulphite (7.6 g in 20 ml water with 416 ml 10 N NaOH; BDH AnalaR #10356.4D; freshly made) and 12 μl of 10 mM Quinol (0.055 g in 50 ml water, BDH AnalR #103122E; freshly made) were added in succession. Quinol is a reducing agent and helps to reduce oxidation of the reagents. Other reducing agents can also be used, for example, dithiothreitol (DTT), mercaptoethanol, quinone (hydroquinone), or other suitable reducing agents. The sample was overlaid with 200 μl of mineral oil. The overlaying of mineral oil prevents evaporation and oxidation of the reagents but is not essential. The sample was then incubated overnight at 55° C. Alternatively the samples can be cycled in a thermal cycler as follows: incubate for about 4 hours or overnight as follows: Step 1, 55° C./2 hr cycled in PCR machine: Step 2, 95° C./2 min. Step 1 can be performed at any temperature from about 37° C. to about 90° C. and can vary in length from 5 minutes to 8 hours. Step 2 can be performed at any temperature from about 70° C. to about 99° C. and can vary in length from about 1 second to 60 minutes, or longer.

After the treatment with Sodium Metabisulphite, the oil was removed, and 1 μl tRNA (20 mg/ml) or 2 μl glycogen were added if the DNA concentration was low. These additives are optional and can be used to improve the yield of DNA obtained by co-precipitating with the target DNA especially when the DNA is present at low concentrations. The use of additives as carrier for more efficient precipitation of nucleic acids is generally desired when the amount nucleic acid is <0.5 μg.

An isopropanol cleanup treatment was performed as follows: 800 μl of water were added to the sample, mixed and then 1 ml isopropanol was added. The water or buffer reduces the concentration of the bisulphite salt in the reaction vessel to a level at which the salt will not precipitate along with the target nucleic acid of interest. The dilution is generally about 1/4 to 1/1000 so long as the salt concentration is diluted below a desired range, as disclosed herein.

The sample was mixed again and left at 4° C. for a minimum of 5 minutes. The sample was spun in a microfuge for 10-15 minutes and the pellet was washed 2× with 70% ETOH, vortexing each time. This washing treatment removes any residual salts that precipitated with the nucleic acids.

The pellet was allowed to dry and then resuspended in a suitable volume of T/E (10 mM Tris/0.1 mM EDTA) pH 7.0-12.5 such as 50 μl. Buffer at pH 10.5 has been found to be particularly effective. The sample was incubated at 37° C. to 95° C. for 1 min to 96 hr, as needed to suspend the nucleic acids.

Addition of Polymerase and Ligase

The polymerase will add the correct base i.e. G (complementary to methylated) or A (complementary to unmethylated).

The ligase will then ligate the G or A base and a circle will be formed.

The bisulphite treated DNA is then degraded with Uracil N DNA glycosylase which also linearises the circle.

The Linear DNA is then amplified with a pair of common primers.

The DNA is then detected on a micro-array platform using a unique DNA sequence (Zip code) present in the clamp primers (NB not detected in traditional way as the Zip code only tells the complex where to go spatially on the array not by hybridization to the complementary strand of the bisulphite treated DNA).

Figure 15:
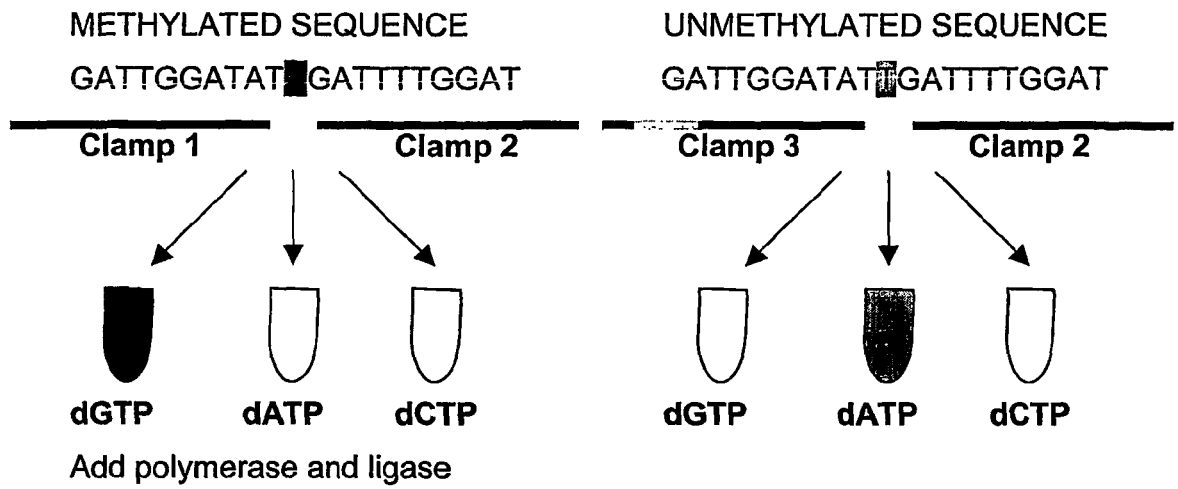
FIG. 15 shows a ligation dependant reaction.

NB Primers 1 and 3 are identical in sequence except for the inclusion of a different zip code (Blue and yellow bars) and primer 1 having a terminal base G which detects the presence of methylation while primer 3 has a terminal base A which detects the lack of methylation. This enables the products to be spatially separated on a micro-array (see FIG. 15). This means that the presence of a C or T can be detected simultaneously in the same reaction vessel. Thus, thousands of different genomic loci can be interrogated in the one reaction vessel and separated on the basis of their unique zip codes.

Figure 16:
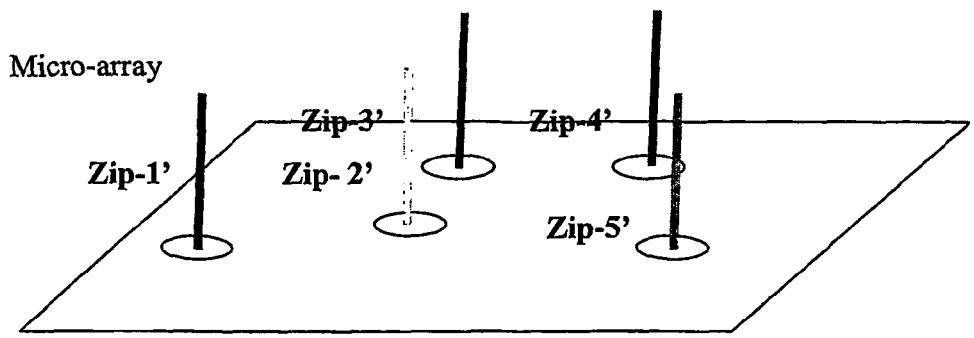
FIG. 16 shows an array tag detection system.

After the clamps have been ligated and amplified they are then directed to specific sites on a micro-array devise predetermined by the internal Zip-code contained within each bisulphite clamp primer set (FIG. 16).

Results

Effect of Exonuclease III Concentration and Ligase Concentration on Clamp Specificity Experiment was carried out using methylated DNA sequences. FIG. 1 shows the effect of ligase enzyme concentration and Exonuclease III concentration of the performance of the clamp reaction. As can be seen from the figure if too much exonuclease enzyme is used (10 Units), the reaction is not as efficient. Conversely if too little enzyme is used (2 Units) then this decreases the specificity of the reaction resulting in non-specific amplification occurring in he A, T and C tracks (see FIG. 1A). The upper band seen if some lanes (indicated by the star) is a dimer of the target band as a results of the polymerase copying the circle twice.

In addition increasing the ligase concentration from 5 U per reaction to 10 U per reaction reduced the specificity of the method again resulting in non-specific detection in the A, T and C tracks (see FIG. 1b). The bolded letters indicate the optimal exonuclease concentrations. One nanogram (ng) of a methylated oligonucleotide was used as a target. Ten ng of each clamp was used in the reaction, together with 0.1 units of Stoffel DNA polymerase. Ampligase enzyme was used at 5 and 10 units. The arrow indicates the correct size of the PCR products.

In detail, the following was added to a 0.5 µl thin-walled PCR tube:

| | |
|---|---|
| 10× Ampligase buffer | 1.0 µl |
| Clamp#1 (10 ng/µl) | 1.0 µl |
| Clamp#2 (10 ng/µl) | 1.0 µl |
| Stoffel Polymerase | 0.1 µl |
| Ampligase | 1.0 µl or 2 µl |
| dG/dA/dT/dC (1 mM) | 1.0 µl (dG/dA/dT/dC are added to separate tubes) |
| water | 3.9 µl or 2.9 µl |

Reactions were incubated as follows:

20° C. 4 min, 95° C. 2 min, 50° C. 15 min, 55° C. 5 min (with a 0.05° C./sec ramp time), 50° C. 1 min.

Exonuclease Treatment:

| | 10U ExoIII/ 2U Exo1 | 5U ExoIII/ 2U Exo1 | 2U ExoIII/ 2U Exo1 |
|---|---|---|---|
| ExoIII | 0.05 µl | 0.025 µl | 0.01 µl |
| ExoI | 0.1 µl | 0.1 µl | 0.1 µl |
| T/E | 0.85 | 0.875 | 0.89 |

One µl of the above reaction mixture was added to the appropriate tubes. The samples then incubated at 37° C. for 14 minutes followed by 2 minutes @ 95° C. and finally 1 minute @ 37° C.

PCR was performed with universal primers by adding the following:

| | |
|---|---|
| 10× PCR buffer | 2.5 µl (Promega) |
| water | 19.0 µl |
| Universal P1 | 1.0 µl |
| Universal P2 | 1.0 µl |
| dNTPs | 1.2 µl |
| Taq | 0.3 µl |
| 95° C. 30 s, 48° C. 45 s, 72° C. 45 s (25 cycles). | |

Detection of Methylated, Unmethylated and a Mixture of 50% Methylated+50% Unmethylated DNA As can be seen from FIG. 2 the system can easily differentiate methylated sequences from unmethylated and can also detect the presence of mixed populations.

One ng of either a methylated oligonucleotide, unmethylated oligo or 50%/50% mixture of methylated and unmethylated oligo was used as a target. Ten ng of each clamp was used in the reaction, together with 1 unit of Stoffel DNA polymerase. Ampligase enzyme was used at 5 units. The arrow indicates the correct size of the PCR products In detail, the following was added to a 0.5 µl thin-walled PCR tube:

| | |
|---|---|
| 10× Ampligase buffer | 1.0 µl |
| Clamp#1 (10 ng/µl) | 1.0 µl |
| Clamp#2 (10 ng/µl) | 1.0 µl |
| Stoffel Polymerase | 0.1 µl (1 Unit) |
| Ampligase | 1.0 µl |
| dG/dA/dT/dC (1 mM) | 1.0 µl (dG/dA/dT/dC are added to separate tubes) |
| water | 3.9 µl |

Reactions were incubated as follows:

20° C. 4 min, 95° C. 2 min, 50° C. 15 min, 55° C. 5 min (with a 0.05° C./sec ramp time), 50° C. 1 min.

Exonuclease Treatment:

| | 5U ExoIII/2U Exo1 |
|---|---|
| ExoIII | 0.025 µl |
| ExoI | 0.1 µl |
| T/E | 0.875 |

One µl of the above reaction mixture was added to the appropriate tubes. The samples then incubated at 37° C. for 14 minutes followed by 2 minutes @ 95° C. and finally 1 minute @ 37° C.

PCR was performed with universal primers by adding the following:

| | |
|---|---|
| 10× PCR buffer | 2.5 µl (Promega) |
| water | 19.0 µl |
| Universal P1 | 1.0 µl |
| Universal P2 | 1.0 µl |
| dNTPs | 1.2 µl |
| Taq | 0.3 µl |
| 95° C. 30 s, 48° C. 45 s, 72° C. 45 s (25 cycles). | |

Effect of Polymerase on the Clamp Reaction

Experiment carried out using methylated DNA sequences.

FIG. 3 shows the effect of different polymerase enzymes on the performance of the reaction. It should be noted that all polymerase enzymes tested produced positive signals when the concentration of the target was further increased. However, not all enzymes could be used at low DNA concentrations without further optimisation.

The results showed that the enzymes that produced the greatest sensitivity were Klenow DNA polymerase and Taq Polymerase. These two enzymes were used subsequently in further experiments.

One ng of each clamp was used in the reaction, together with 1 units of DNA polymerase. The arrow indicates the correct size of the PCR products.

In detail, the following was added to a 0.5 µl thin-walled PCR tube:

| | |
|---|---|
| 10× Ampligase buffer | 1.0 µl |
| Clamp#1 (1 ng/µl) | 1.0 µl |
| Clamp#2 (1 ng/µl) | 1.0 µl |
| Polymerase | 1U |
| Ampligase | 5U |
| dG/dA/dT (1 mM) | 1.0 µl (dG/dA/dT are added to separate tubes) |
| water | 3.9 µl |

Template DNA was added at the appropriate concentrations indicated above.

Reactions were incubated as follows:

20° C. 4 min, 95° C. 2 min, 50° C. 15 min, 55° C. 5 min (with a 0.05° C./sec ramp time), 50° C. 1 min.

Exonuclease Treatment:

| | 5U ExoIII/2U ExoI |
|---|---|
| ExoIII | 0.025 µl |
| ExoI | 0.1 µl |
| T/E | 0.875 |

One µl of the above reaction mixture was added to the appropriate tubes. The samples then incubated at 37° C. for 14 minutes followed by 2 minutes @ 95° C. and finally 1 minute @ 37° C.

0.5 µl of uracil DNA glycosylase was added to each reaction tube and the samples incubated as follows; 50° C. 15 min, 95° C. 5 min, 50° C. 1 min.

PCR was performed with universal primers by adding the following:

| | |
|---|---|
| 10× PCR buffer | 2.5 µl (Promega) |
| water | 19.0 µl |
| Universal P1 | 1.0 µl |
| Universal P2 | 1.0 µl |
| dNTPs | 1.2 µl |
| Taq | 0.3 µl |
| 95° C. 30 s, 48° C. 45 s, 72° C. 45 s (25 cycles). | |

Effect of Polymerase/Ligase Concentration

Experiment carried out using methylated DNA

Figure 4:
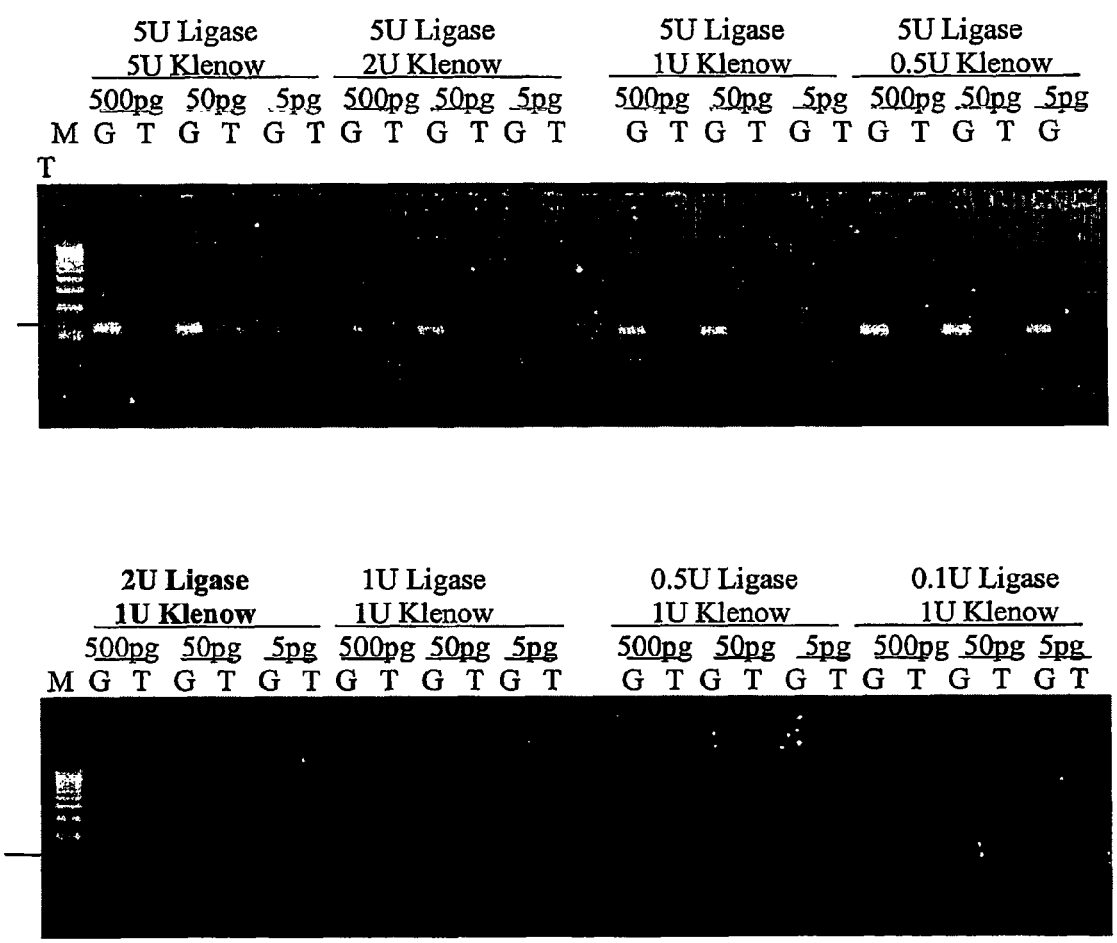
FIG. 4 shows effect of Polymerase/Ligase concentration (according to sixth aspect).

FIG. 4 shows that high concentrations of both enzymes can produce false positive signals such as those seen with 5 Units of both ligase and polymerase where bands are present in both the G and T tracks. Whereas using 2 Units ligase and 1 Unit polymerase a band is only present in the correct G track. Careful titration of the enzyme combinations is therefore essential to produce the most sensitive and specific enzyme combinations. As can be seen 2 U of ligase and 1 U of Klenow gave the most consistent and reliable amplification even at low DNA concentrations.

One ng of each clamp was used in the reaction, together with the Ampligase and polymerase enzyme were used as above. The arrow indicates the correct size of the PCR products.

In detail, the following was added to a 0.5 µl thin-walled PCR tube:

| | |
|---|---|
| 10× Ampligase buffer | 1.0 µl |
| Clamp#1 (1 ng/µl) | 1.0 µl |
| Clamp#2 (1 ng/µl) | 1.0 µl |
| Klenow | as above |
| Ampligase | as above |
| dG/dT (1 mM) | 1.0 µl (dG/dT are added to separate tubes) |
| water | 3.9 µl |

Template DNA was added at the appropriate concentrations indicated above. Reactions were incubated as follows:

20° C. 4 min, 95° C. 2 min, 50° C. 15 min, 55° C. 5 min (with a 0.05° C./sec ramp time), 50° C. 1 min.

Exonuclease Treatment:

| | 5U ExoIII/2U ExoI |
|---|---|
| ExoIII | 0.025 µl |
| ExoI | 0.1 µl |
| T/E | 0.875 |

One µl of the above reaction mixture was added to the appropriate tubes. The samples then incubated at 37° C. for 14 minutes followed by 2 minutes @ 95° C. and finally 1 minute @ 37° C.

0.5 µl of uracil DNA glycosylase was added to each reaction tube and the samples incubated as follows; 50° C. 15 min, 95° C. 5 min, 50° C. 1 min.

PCR was performed with universal primers by adding the following:

| | |
|---|---|
| 10× PCR buffer | 2.5 µl (Promega) |
| water | 19.0 µl |
| Universal P1 | 1.0 µl |
| Universal P2 | 1.0 µl |
| dNTPs | 1.2 µl |
| Taq | 0.3 µl |
| 95° C. 30 s, 48° C. 45 s, 72° C. 45 s (25 cycles). | |

Figure 5:
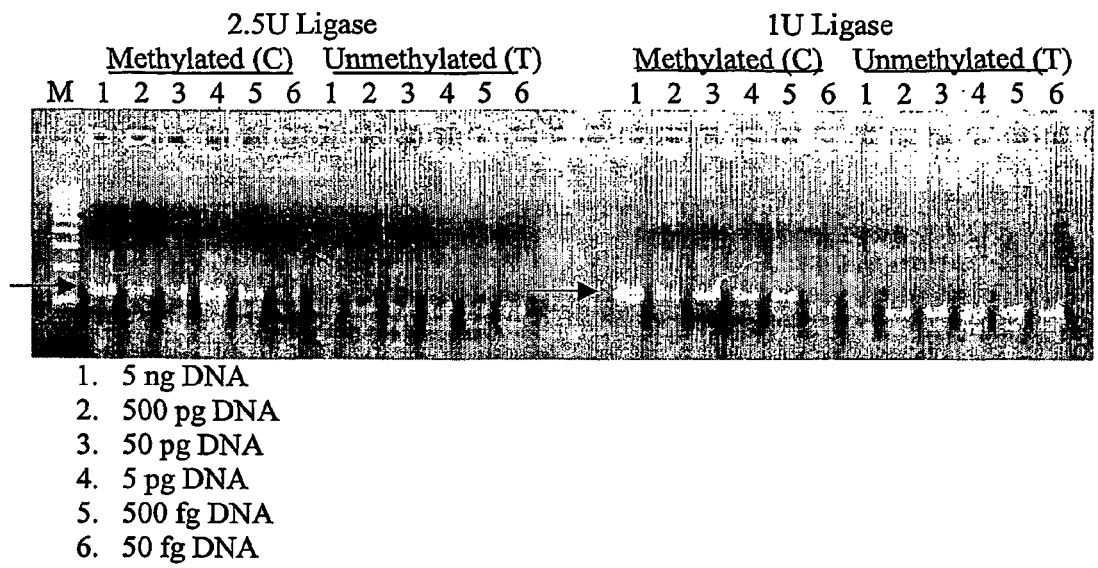
FIG. 5 shows sensitivity of the Clamp reaction (according to third aspect) using clamp primers directed against methylated DNA sequences.

Sensitivity of the Clamp Reaction Using Clamp Primers Directed Against Methylated DNA Sequences As can be seen from FIG. 5, the assay had very high specificity and sensitivity at all DNA concentrations tested.

One ng of each clamp was used in the reaction, together with the Ampligase enzyme was used at 2.5 and 1 units. The arrow indicates the correct size of the PCR products.

In detail, the following was added to a 0.5 µl thin-walled PCR tube:

| | |
|---|---|
| 10× Ampligase buffer | 1.0 µl |
| Clamp#1 (1 ng/µl) | 1.0 µl |
| Clamp#2 (1 ng/µl) | 1.0 µl |
| Clamp#3 (1 ng/µl) | 1.0 µl |
| Ampligase | 0.5 or 0.2 µl |
| water | 4.5 or 4.8 µl |

One µl of template DNA was added at the appropriate concentrations indicated above.

Reactions were incubated as follows:

20° C. 4 min, 95° C. 2 min, 50° C. 15 min, 55° C. 5 min (with a 0.05° C./sec ramp time), 50° C. 1 min.

Exonuclease treatment:

| | 5U ExoIII/2U Exo1 |
|---|---|
| ExoIII | 0.025 µl |
| ExoI | 0.1 µl |
| T/E | 0.875 |

One µl of the above reaction mixture was added to the appropriate tubes. The samples then incubated at 37° C. for 14 minutes followed by 2 minutes @ 95° C. and finally 1 minute @ 37° C.

0.5 µl of uracil DNA glycosylase was added to each reaction tube and the samples incubated as follows; 50° C. 15 min, 95° C. 5 min, 50° C. 1 min.

PCR was performed with universal primers by adding the following:

| | |
|---|---|
| 10× PCR buffer | 2.5 µl (Promega) |
| water | 19.0 µl |
| Universal P1 | 1.0 µl |
| Universal P2 | 1.0 µl |
| dNTPs | 1.2 µl |
| Taq | 0.3 µl |
| 95° C. 30 s, 48° C. 45 s, 72° C. 45 s (25 cycles). | |

Clamp Reaction on Genomic DNA (Known to be Unmethylated at the Site of Interrogation)

Figure 6:
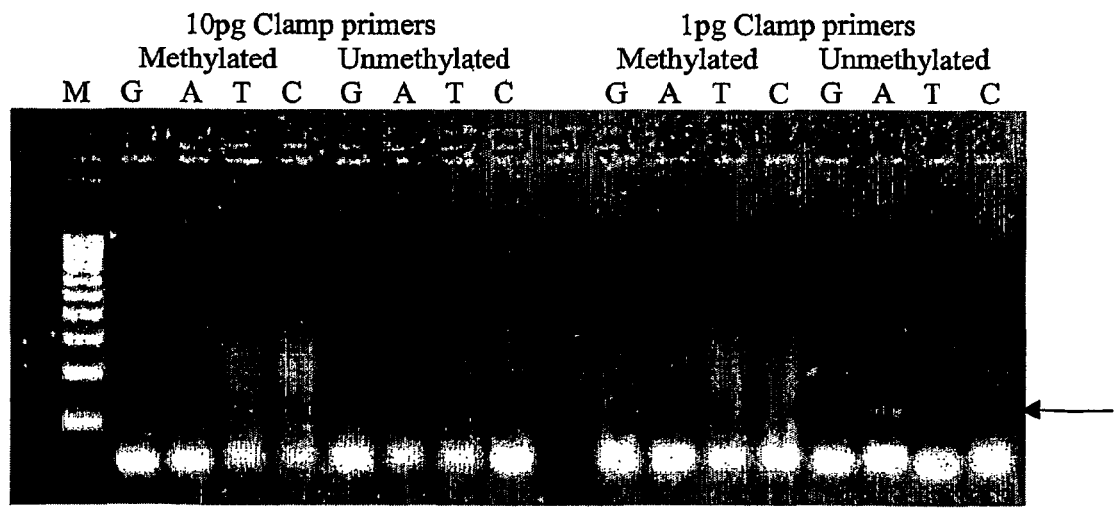
FIG. 6 shows clamp reaction on genomic DNA (known to be unmethylated at the site of interrogation) (according to sixth aspect).

Ten pg or 1 pg of each clamp was used in the reaction, together with the ampligase enzyme at 2.5 and 1 units. The arrow indicates the correct size of the PCR products (FIG. 6).

In detail, the following was added to a 0.5 µl thin-walled PCR tube:

| | |
|---|---|
| 10× Ampligase buffer | 1.0 µl |
| Clamp#1 | 1.0 µl |
| Clamp#2 | 1.0 µl |
| Ampligase | 0.5 µl |
| Polymerase | 0.1 µl |
| dG/dA/dT/dC (1 mM) | 1.0 µl (dG/dA/dT/dC are added to separate tubes) |
| water | 4.4 µl |

One µl of bisulphite template DNA was added.

Reactions were incubated as follows:

20° C. 4 min, 95° C. 2 min, 50° C. 15 min, 55° C. 5 min (with a 0.05° C./sec ramp time), 50° C. 1 min.

Exonuclease treatment:

| | 5U ExoIII/2U Exo1 |
|---|---|
| ExoIII | 0.025 µl |
| ExoI | 0.1 µl |
| T/E | 0.875 |

One µl of the above reaction mixture was added to the appropriate tubes. The samples then incubated at 37° C. for 14 minutes followed by 2 minutes @ 95° C. and finally 1 minute @ 37° C.

0.5 µl of uracil DNA glycosylase was added to each reaction tube and the samples incubated as follows; 50° C. 15 min, 95° C. 5 min, 50° C. 1 min.

PCR was performed with universal primers by adding the following:

| | |
|---|---|
| 10× PCR buffer | 2.5 µl (Promega) |
| water | 19.0 µl |
| Universal P1 | 1.0 µl |
| Universal P2 | 1.0 µl |
| dNTPs | 1.2 µl |
| Taq | 0.3 µl |
| 95° C. 30 s, 48° C. 45 s, 72° C. 45 s (40 cycles). | |

Clamp Reaction—Non-circular

Figure 7:
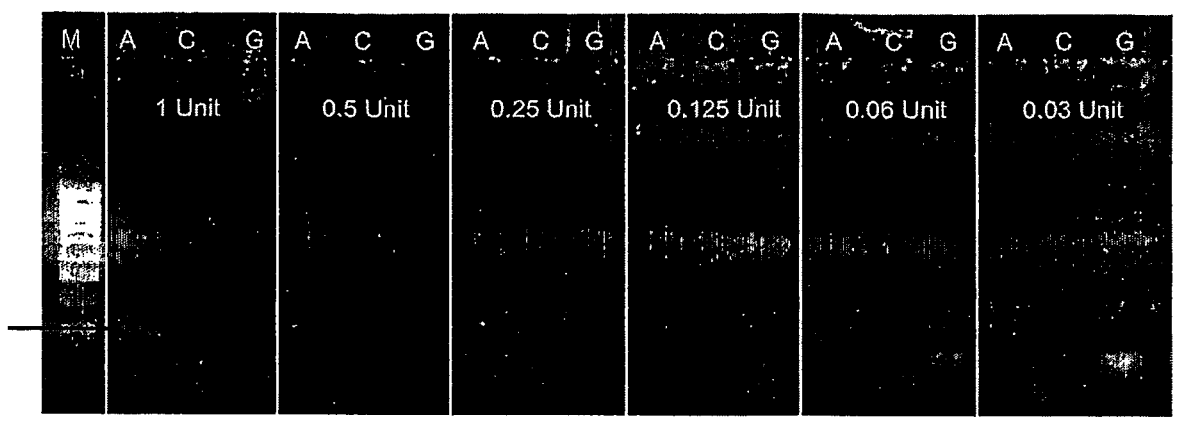
FIG. 7 shows clamp reaction (according to second aspect).

FIG. 7 shows the results of a ligase fill reaction using 2 single arms of two clamps.

Five pg of a uracil containing oligonucleotide (unmethylated) was used as a target. One fmol of each oligo "arm" was used in the reaction, together with 0.05 units of Taq polymerase. Ampligase enzyme was diluted from 1 unit to 0.03 unit. The arrow indicates the correct size of the PCR products.

In detail, the following was added to a 0.5 µl thin-walled PCR tube:

| | |
|---|---|
| 10× Ampligase buffer | 0.9 µl |
| Oligo target (5 pg/µl) | 1.0 µl |
| Clamp 1 (1 fmol/µl) | 1.0 µl |
| Clamp 2 (1 fmol/µl) | 1.0 µl |
| Taq Polymerase | 0.1 µl (of a 0.5 U/µl stock diluted in Ampligase buffer) |
| dA/dC/dG (1 mM) | 1.0 µl (dA/dC/dG are added to separate tubes) |
| water | 4.0 µl |

Reactions were incubated as follows:

20° C. 4 min, 95° C. 5 min, 60° C. 25 min, 65° C. 5 min (with a 0.05° C./sec ramp time), 50° C. 1 min.

One µl of UDG was added at this point to degrade the template.

50° C. 15 min, 95° C. 5 min, 50° C. 1 min.

PCR was performed with universal primers by adding the following:

| | |
|---|---|
| 10× PCR buffer | 2.5 µl (Promega) |
| water | 19.0 µl |
| Universal P1 | 1.0 µl |
| Universal P2 | 1.0 µl |
| dNTPs | 1.2 µl |

-continued

Taq 0.3 µl
95° C. 30 s, 48° C. 45 s, 72° C. 45 s (28 cycles).

First Aspect Examples

FIG. 8 show the method according to the first aspect of the present invention. In Example #1 and #2, the two adjacent clamp sequences were then ligated together using a DNA ligase.

Second Aspect Examples

FIG. 9 shows the method according to the second aspect of the present invention. In Example #3, a polymerase enzyme will bring the correct base (G) to the site and then a ligase enzyme will ligate the base into the DNA sequence to form a linear probe. In Example #4, a polymerase enzyme will bring the correct base (A) to the site and then a ligase enzyme will ligate the base into the DNA sequence to form a linear probe.

Third Aspect Examples

In Example #5, four independent hybridisation events need to occur to bring the three clamp sequences positioned correctly on the bisulphite treated genomic DNA (FIG. 10). One arm of the clamps now form a semi-circular probe, while the other two clamps hybridise to the top and bottom strands of the DNA adjacent to the semi-circular probe. A ligase enzyme will ligate the base into the DNA sequence to form a fully linearised probe.

In Example #6, four independent hybridisation events need to occur to bring the three clamp sequences positioned correctly on the bisulphite treated genomic DNA (FIG. 10). One arm of the clamps now form a semi-circular probe, while the other two clamps hybridise to the top and bottom strands of the DNA adjacent to the semi-circular probe. A ligase enzyme will ligate the base into the DNA sequence to form a fully linearised probe.

Fourth Aspect Examples

In Example #7, four independent hybridisation events need to occur to bring the three clamp sequences positioned correctly on the bisulphite treated genomic DNA (FIG. 11). One arm of the clamp now forms a semi-circle probe, while the other two clamps hybridise to the top and bottom strands of the DNA adjacent to the semi-circular probe. A polymerase enzyme will bring the correct base (G) to the site and then a ligase enzyme will ligate the base into the DNA sequence to form a fully linearised probe.

In Example #8, four independent hybridisation events need to occur to bring the three clamp sequences positioned correctly on the bisulphite treated genomic DNA (FIG. 11). One arm of the clamp now form a semi-circle probe, while the other two clamps hybridise to the top and bottom strands of the DNA adjacent to the semi-circular probe. A polymerase enzyme will bring the correct base (A) to the site and then a ligase enzyme will ligate the base into the DNA sequence to form a fully linearised probe.

Fifth Aspect Examples

In Example #9, four independent hybridisation events need to occur to bring the two clamp sequences positioned correctly on the bisulphite treated genomic DNA. Each arm of the clamps now form a semi-circle probe (FIG. 12). A ligase enzyme will ligate the bases into the DNA sequence to form a fully circularised probe.

In Example #10, four independent hybridisation events need to occur to bring the two clamp sequences positioned correctly on the bisulphite treated genomic DNA. Each arm of the clamp probes now form a semi-circle (FIG. 12). A ligase enzyme will ligate the base into the DNA sequence to form a fully circularised probe.

Sixth Aspect Examples

In Example #11, four independent hybridisation events need to occur to bring the two clamp sequences positioned correctly on the bisulphite treated genomic DNA. Each arm of the clamps now forms a semi-circle probe (FIG. 13). A polymerase enzyme will bring the correct base (G) to the site and then a ligase enzyme will ligate the two semi-circular probes to from a fully circularised probe.

In Example #12, four independent hybridisation events need to occur to bring the two clamp sequences positioned correctly on the bisulphite treated genomic DNA (FIG. 13). Each arm of the clamps now form a semi-circle probes. A polymerase enzyme will bring the correct base (A) to the site and then a ligase enzyme ligate the two semi-circular probes to from a fully circularised probe.

Figure 14:
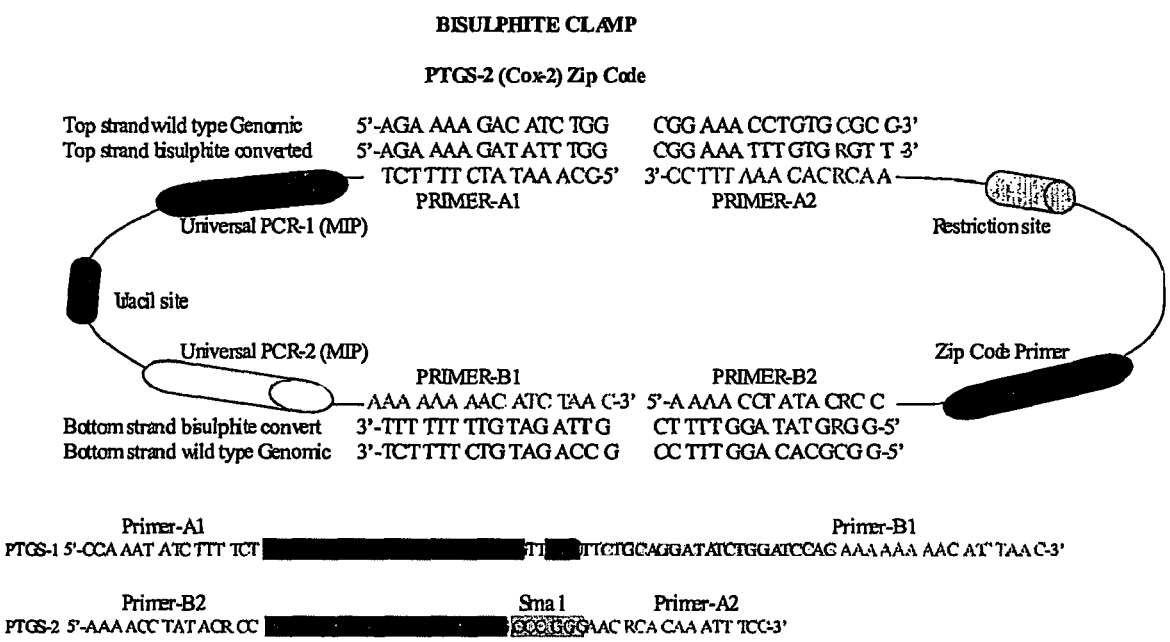
FIG. 14 is a schematic representation of the Bisulphite Clamp method according to the present invention.

FIG. 14 shows a schematic example of a clamp reaction forming a circular probe with a uracil cleavage site.

Array Tag Detection System

The bisulphite clamp is a new method for genome wide detection of methylated cytosine bases. Unlike all previous methods for the detection of methylated cytosines, the clamp method does not depend on the amplification of the bisulphite treated nucleic acid. The method is unique in that it can use a ligation reaction to determine the presence or absence of a methylated cytosine within a CpG doublet (see FIGS. 15 and 16). This means that individual CpG sites can be analysed throughout the genome.

After the clamps have been ligated and amplified they can then directed to specific sites on a micro-array devise predetermined by the internal Zip-code contained within each bisulphite clamp primer set. FIG. 16 shows an example of such a detection system.

One of the major advantages of this approach over conventional micro-array analysis is that the hybridisation conditions can be controlled in a precise manner. The zip code primers can be tailor made so that they all share the same melting temperatures and have similar sequence content. This means that the hybridisation kinetics will be very similar for each probe, whereas in conventional micro-array the hybridisations are dependant on the DNA sequence of the genomic nucleic acid and cannot be controlled in the same manner.

SUMMARY

There are a number of unique advantages to the bisulphite clamp method according to the present invention for the genome wide detection of methylation states compared to existing technologies. One major advantage is the exquisite specificity generated during the reaction. Conventional bisulphite analysis (Clark et al, 1994) relies on two rounds of nested PCR to generate the specificity required in a bisulphite converted genome. This is due to the fact that after bisulphite treatment the genome is essentially composed of only three bases namely A G and T since all the unmethylated cytosines have been converted to U. Four nested primers are then designed to one of the bisulphite treated strands of DNA then two rounds of PCR are performed to generate the necessary specificity and sensitivity. After bisulphite treatment, the two strands of DNA are no longer complementary. The targeting of both strands after conversion has to date not been utilised. The bisulphite clamp methodology according to the present invention can target both strands of the modified or converted DNA (see FIG. 1), thus four independent hybridization reactions need to occur before the reaction will proceed. This in effect gives nested PCR specificity in one round reducing the chances of PCR contamination and greatly simplifying the procedure. In addition, non-specific amplification often occurs especially when the amount of target DNA is low. This is due to the nature of the PCR amplification reaction. The bisulphite clamp method, however, overcomes this by the use of a dual specificity system. The first layer of specificity is generated by the polymerase filling in the correct base. Even if the polymerase makes an error, the second round of fidelity is achieved by the use of a ligase enzyme which means that any incorrect base will not be correctly ligated and the reaction will come to a halt.

Another feature of the bisulphite clamp method can be the incorporation of a uracil site into one arm of one primer. Thus, when the correct hybridisation and ligation occurs a circle is formed. The reaction mix can then be treated with Uracil N Glycosylase (UNG). This enzyme will then degrade all the uracil-containing bisulphite treated DNA and at the same time linearise the circle. Thus, subsequent amplification now occurs in a pure population of target molecules greatly increasing the efficiency of the reaction unlike conventional PCR which occurs in a sea of non target genomic DNA. Alternatively, a unique restriction site can be added to one of the clamp primers so that after UNG digestion, the circles remain undigested but the bisulphite treated genomic DNA has been degraded. The circular DNA can then be replicated by isothermal Rolling Circle Amplification (RCA) (Lizardi et al. Mutation detection and single-molecule counting using isothermal rolling-circle amplification. 1998 Nat. Genetics (19); 225-232).

Further, the bisulphite clamp method allows the multiplexing of a large number of probes in the same reaction tube. Thus, large numbers of genomic regions can be interrogated simultaneously in the one reaction tube. This is due to the fact that the clamps can contain common PCR primer sites, thus only two primers are required to amplify the target circularized molecules unlike multiplex PCR where individual primer sets need to be designed to each loci of interest.

In addition, the method also eliminates the problem of PCR bias which can often occur in a bisulphite reaction. This is a result of the fact that the bisulphite clamp does not depend on the amplification of a genomic region spanning two primers sites. It has been shown that amplification of certain sequences of bisulphite treated DNA can lead to an underestimation of the true methylation status (Warneke et al). This phenomenon is a consequence of the differing sequence content of a methylated DNA strand compared to an unmethylated strand, resulting in the preferential copying of the unmethylated strand over the methylated strand. As the clamp only depends on a hybridization reaction, PCR bias will not occur.

Moreover, the detection of methylation changes in bisulphite treated DNA by micro-arrays has relied on sequence specific hybridisation of regions of amplified DNA contained between two unique primer sites. As stated previously, the sequence content of a methylated DNA sequence is very different from an unmethylated sequence. This has the effect that the hybridisation kinetics of an unmethylated sequence will be very different to that of a methylated sequence. Thus, in practical terms, it is very difficult to determine hybridisation conditions that will favour both the binding of the unmethylated sequence and the methylated sequence to an array simultaneously to the same array. The bisulphite clamp procedure can overcome this problem by optionally incorporating zip-code sequence into the primers that subsequently direct the sequence to a defined place on an array. The zipcode sequence is not designed to correspond with a piece of bisulphite treated DNA but a randomly defined DNA sequence that is not present in the human genome. This zipcode sequence can be "shuffled" so that each zip code has the same melting temperature and sequence composition. Thus, the hybridisation conditions in the bisulphite clamp can be tailor made so that the kinetics of hybridisation of each probe will be identical. Thus the final read out will be a true reflection of the methylation status of the sample.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for determining the methylation status of a potential methylation site in genomic nucleic acid comprising:
   treating genomic nucleic acid with an agent which modifies cytosine bases but does not modify 5-methyl-cytosine bases under conditions to form a modified nucleic acid template from two complementary strands of genomic nucleic acid containing a potential methylation site;
   providing a first clamp containing a first capture sequence and a second capture sequence, first capture sequence being complementary to a region flanking one side of the potential methylation site in the first strand of the modified nucleic acid template, and the second capture sequence being complementary to a region flanking one side of the potential methylation site in the second strand of the modified nucleic acid template;
   providing a second clamp containing a third capture sequence complementary to a region flanking the other side of the potential methylation site in the modified nucleic acid template;
   allowing the first clamp and the second clamp to hybridise to the modified nucleic acid template;
   ligating the hybridised first and second clamps to form a probe spanning the potential methylation site in the modified nucleic acid template;
   digesting the modified nucleic acid template to obtain the probe; and
   detecting the probe and determining the methylation status of the potential methylation site in the modified genomic nucleic acid.

2. The method according to claim 1 wherein the first clamp and the second clamp hybridise to the modified nucleic acid template such that there is no complementary bases at the potential methylation site and causing at least one base to be inserted between the first clamp and the second clamp prior to ligating the clamps to form a probe spanning the potential methylation site in the modified nucleic acid template.

3. The method according to claim 1 wherein the potential methylation site is cytosine (C) flanked 3' by a guanine (G).

4. The method according to claim 1 wherein the modifying agent is selected from the group consisting of bisulfite, acetate, and citrate.

5. The method according to claim 4 wherein the modifying agent is sodium bisulfite.

6. The method according to claim 1 wherein at least one of the first or second clamps contains a universal primer which allows amplification of the probe after the ligation step.

7. The method according to claim 1 wherein at least one of the first or second clamps contains a capture site which allows capture of the probe.

8. The method according to claim 1 wherein at least one of the first or second clamps contains a cleavable site.

9. The method according to claim 8 wherein the cleavable site is nuclease restriction site.

10. The method according to claim 9 wherein the cleavable site is a uracil base.

11. The method according to claim 1 wherein the complementary sequences of the first or second clamps when ligated span the potential methylation site on the modified nucleic acid template.

12. The method according claim 1 wherein the clamps are ligated using a suitable enzyme capable of ligating single stranded nucleic acid.

13. The method according to claim 1 wherein the clamps are ligated at or near the first and second capture sequences.

14. The method according claim 2 wherein one or more bases are inserted between the clamps using a nucleic acid polymerase.

15. The method according to claim 14 wherein the base insertion reaction is carried out in the presence of a single nucleotide type and each nucleotide type is reacted separately such that the insertion of a particular base will be indicative of the identity of the complementary base on the modified nucleic acid template.

16. The method according to claim 1 wherein the modified nucleic acid template is digested by an enzyme.

17. The method according to claim 16 wherein the enzyme is Uracil N DNA Glycosylase.

18. The method according to claim 1 wherein the probe is detected and the methylation status of the potential methylation site in the modified genomic nucleic acid determined with a detection system which can recognise incorporation of the missing base(s) between the first and second clamps, or detect specific amplification of the probe.

19. The method according to claim 18 wherein the detection system is selected from the group consisting of hybridization by array, Southern blot type detection, Real-Time PCR quantitation, fluorescent beads, enzyme conjugates, radioactive beads, ligase chain reaction, and isothermal DNA amplification.

20. The method according to claim 1 wherein the genomic nucleic acid is DNA.

21. A method for determining the methylation status of a potential methylation site on genomic nucleic acid comprising:
   treating genomic nucleic acid with an agent which modifies cytosine bases but does not modify 5-methyl-cytosine bases under conditions to form a modified nucleic acid template from two complementary strands of genomic nucleic acid containing a potential methylation site;
   providing a first clamp containing a first capture sequence and a second capture sequence, first capture sequence being complementary to a region flanking one side of the potential methylation site in the first strand of the modified nucleic acid template, and the second capture sequence being complementary to a region flanking one side of the potential methylation site in the second strand of the modified nucleic acid template;
   providing a second clamp containing a third capture sequence and a fourth capture sequence, the third capture sequence being complementary to a region flanking the other side the potential methylation site in the first strand of the modified nucleic acid template, and the fourth capture sequence being complementary to a region flanking the other side of the potential methylation site in the second strand of the modified nucleic acid template;
   allowing the first clamp and the second clamp to hybridise to the two complementary strands of the modified nucleic acid template;
   ligating the hybridised clamps to form a circular probe spanning the potential methylation site in the complementary strands of the modified nucleic acid template;
   digesting the modified nucleic acid template to obtain the circular probe; and
   detecting the circular probe and determining the methylation status of the potential methylation site in the modified genomic nucleic acid.

22. The method according to claim 21 wherein the first clamp and the second clamp hybridise to the two complementary strands of the modified nucleic acid template such that there is no complementary bases at the potential methylation site of at least one of the complementary strands of the modified nucleic acid template, and causing at least one base to be inserted between the first clamp and the second clamp prior to ligating the clamps to form a probe spanning the potential methylation site in the modified nucleic acid template.

23. The method according to claim 21 wherein the potential methylation site is cytosine (C) flanked 3' by a guanine (G).

24. The method according to claim 21 wherein the modifying agent is selected from the group consisting of bisulfite, acetate, and citrate.

25. The method according to claim 23 wherein the modifying agent is sodium bisulfite.

26. The method according to claim 21 wherein at least one of the first or second clamps contains a universal primer which allows amplification of the probe after the ligation step.

27. The method according to claim 21 wherein at least one of the first or second clamps contains a capture site which allows capture of the probe.

28. The method according to claim 21 wherein at least one of the first or second clamps contains a cleavable site.

29. The method according to claim 28 wherein the cleavable site is nuclease restriction site.

30. The method according to claim 28 wherein the cleavable site is a uracil base.

31. The method according to claim 21 wherein the complementary sequences of the first or second clamps when ligated span the potential methylation site on the modified nucleic acid template.

32. The method according to claim 21 wherein the clamps are ligated using a suitable enzyme capable of ligating single stranded nucleic acid.

33. The method according to claim 21 wherein the clamps are ligated at or near the first and second capture sequences.

34. The method according to claim 22 wherein one or more bases are inserted between the clamps using a DNA polymerase.

35. The method according to claim 34 wherein the base insertion reaction is carried out in the presence of a single nucleotide type and each nucleotide type is reacted separately such that the insertion of a particular base will be indicative of the identity of the complementary base on the modified nucleic acid template.

36. The method according to claim 21 wherein the modified nucleic acid template is digested by an enzyme.

37. The method according to claim 36 wherein the enzyme is Uracil N DNA Glycosylase.

38. The method according to claim 21 wherein the probe is detected and the methylation status of the potential methylation site in the modified genomic nucleic acid determined with a detection system which can recognise incorporation of the missing base(s) between the first and second clamps, or detect specific amplification of the probe.

39. The method according to claim 38 wherein the detection system is selected from the group consisting of hybridization by array, Southern blot type detection, Real-Time PCR quantitation, fluorescent beads, enzyme conjugates, radioactive beads, ligase chain reaction, and isothermal DNA amplification technologies including strand displacement amplification or rolling circle amplification.

40. The method according to claim 21 wherein the genomic nucleic acid is DNA.

41. The method according to claim 19, wherein the isothermal DNA amplification is strand displacement amplification or rolling circle amplification.

* * * * *